United States Patent
Chen et al.

(10) Patent No.: US 7,855,223 B2
(45) Date of Patent: *Dec. 21, 2010

(54) METHOD OF TREATING INFLAMMATORY ARTHRITIS

(75) Inventors: Ruihuan Chen, Palo Alto, CA (US); Simon K. Mencher, New York, NY (US); Allen Tsao, Windlake, WI (US); Xiao Mei Liu, Flushing, NY (US); Longgui Wang, Flushing, NY (US)

(73) Assignee: Natrogen Therapeutics International, Inc., New York, NY (US)

( * ) Notice: Subject to any disclaimer, the term of this patent is extended or adjusted under 35 U.S.C. 154(b) by 271 days.

This patent is subject to a terminal disclaimer.

(21) Appl. No.: 11/494,362

(22) Filed: Jul. 26, 2006

(65) Prior Publication Data

US 2007/0027203 A1    Feb. 1, 2007

Related U.S. Application Data

(63) Continuation-in-part of application No. 10/754,547, filed on Jan. 12, 2004, now abandoned.

(51) Int. Cl.
*A61K 31/40* (2006.01)
*A61K 31/405* (2006.01)
*A61K 31/56* (2006.01)
*A61K 31/19* (2006.01)

(52) U.S. Cl. .............. 514/414; 514/415; 514/416; 514/23; 514/159; 514/171; 514/570; 514/254.09

(58) Field of Classification Search ........... 514/414, 514/825, 254.09, 415, 416, 171, 570, 159
See application file for complete search history.

(56) References Cited

U.S. PATENT DOCUMENTS

| | | | |
|---|---|---|---|
| 3,995,030 A | 11/1976 | Malachowski | 424/127 |
| 4,113,881 A | 9/1978 | Diehl | 424/312 |
| 4,118,484 A | 10/1978 | Wechter et al. | 424/180 |

(Continued)

FOREIGN PATENT DOCUMENTS

DE    100 53 474    5/2002

(Continued)

OTHER PUBLICATIONS

Nonomura et al. Suppression of arthritis by forced expression of cyclin-dependent kinase inhibitor p21cip1 gene into the joints, International Immunology, Jun. 2001, vol. 13, No. 6 pp. 723-731.*

(Continued)

*Primary Examiner*—Yvonne L Eyler
*Assistant Examiner*—Donna Jagoe
(74) *Attorney, Agent, or Firm*—Fennemore Craig, P.C.

(57) ABSTRACT

The present invention is directed to a method for treating inflammatory arthritis in a mammal. The method typically comprises administering to an animal a therapeutically effective amount of at least one compound selected from indigo, isoindigo, indirubin or derivatives thereof, such as NATURA-α or NATURA. The present invention is further directed to pharmaceutical compositions that include a therapeutically effective amount of at least one compound of the invention, an anti-inflammatory arthritis agent and a pharmaceutically acceptable carrier.

13 Claims, 9 Drawing Sheets

U.S. PATENT DOCUMENTS

| | | | |
|---|---|---|---|
| 4,172,889 A | 10/1979 | Wechter et al. | 424/180 |
| 4,176,179 A | 11/1979 | Gainer | 424/180 |
| 4,322,405 A | 3/1982 | Schulthess et al. | 424/93 |
| 4,375,468 A | 3/1983 | Dunn | 424/230 |
| 4,468,398 A | 8/1984 | Johnson et al. | 424/250 |
| 4,500,533 A | 2/1985 | Matsumoto | 514/256 |
| 4,525,345 A | 6/1985 | Dunn et al. | 424/22 |
| 4,533,551 A | 8/1985 | Martel | 514/411 |
| 4,732,752 A | 3/1988 | Stephan | 424/85 |
| 4,968,510 A | 11/1990 | Jensen | 424/630 |
| 5,026,538 A | 6/1991 | Lieberman et al. | 424/1.1 |
| 5,061,475 A | 10/1991 | Lieberman et al. | 424/1.1 |
| 5,061,724 A | 10/1991 | Gertner | 514/62 |
| 5,098,899 A | 3/1992 | Gilbert et al. | 514/167 |
| 5,149,688 A * | 9/1992 | Ando et al. | 514/251 |
| 5,342,615 A | 8/1994 | Nakai et al. | 424/85.2 |
| 5,389,617 A | 2/1995 | Drell | 514/43 |
| 5,399,347 A | 3/1995 | Trentham et al. | 424/184.1 |
| 5,511,563 A | 4/1996 | Diamond | 128/848 |
| 5,567,409 A | 10/1996 | Aizawa et al. | 424/9.363 |
| 5,696,092 A | 12/1997 | Pattierno et al. | 514/21 |
| 5,720,955 A | 2/1998 | Weiner et al. | 424/184.1 |
| 5,770,357 A | 6/1998 | Douvas et al. | 435/5 |
| 5,782,792 A | 7/1998 | Jones et al. | 604/5 |
| 5,783,188 A | 7/1998 | Weiner et al. | 424/184.1 |
| 5,843,445 A | 12/1998 | Weiner et al. | 424/184.1 |
| 5,843,919 A | 12/1998 | Burger | 514/62 |
| 5,849,323 A | 12/1998 | Braswell et al. | 424/439 |
| 5,849,336 A | 12/1998 | Aoyagi et al. | 424/570 |
| 5,856,446 A | 1/1999 | Weiner et al. | 530/356 |
| 5,905,083 A | 5/1999 | Cincotta et al. | 514/288 |
| 5,952,367 A | 9/1999 | Pak | 514/420 |
| 6,033,672 A | 3/2000 | Douvas et al. | 424/208.1 |
| 6,040,306 A | 3/2000 | Batts et al. | 514/236.8 |
| 6,083,906 A | 7/2000 | Troutt | 514/2 |
| 6,087,382 A | 7/2000 | Bonner, Jr. et al. | 514/356 |
| 6,197,776 B1 | 3/2001 | Bonner, Jr. et al. | 514/262 |
| 6,204,242 B1 | 3/2001 | Bae et al. | 514/2 |
| 6,346,519 B1 | 2/2002 | Petrus | 514/62 |
| 6,353,024 B1 | 3/2002 | Grouhel et al. | 514/534 |
| 6,369,082 B1 * | 4/2002 | Lacombe et al. | 514/333 |
| 6,372,794 B1 | 4/2002 | Nimni | 514/578 |
| 6,465,473 B1 | 10/2002 | Bonner, Jr. et al. | 514/262 |
| 6,566,341 B1 * | 5/2003 | Wang et al. | 514/25 |
| 6,610,728 B2 | 8/2003 | Macias | 514/419 |
| 6,613,800 B1 | 9/2003 | Smith | 514/494 |
| 6,656,925 B2 | 12/2003 | Petrus | 514/62 |
| 6,933,315 B2 | 8/2005 | Wang et al. | 514/414 |
| 7,098,184 B2 | 8/2006 | Godfrey et al. | 514/2 |
| 2002/0132792 A1 | 9/2002 | Prien et al. | 514/63 |
| 2005/0090426 A1* | 4/2005 | Blumberg | 514/2 |
| 2005/0154046 A1* | 7/2005 | Wang et al. | 514/414 |
| 2005/0197381 A1 | 9/2005 | Wang et al. | 514/414 |

FOREIGN PATENT DOCUMENTS

| | | |
|---|---|---|
| EP | 0 987 027 | 3/2000 |
| JP | 61007254 | 1/1986 |
| WO | WO 99/62503 | 12/1999 |
| WO | WO 00/61124 | 10/2000 |
| WO | WO 00/61555 | 10/2000 |
| WO | WO/02/074742 | 9/2002 |
| WO | WO/02/092079 | 11/2002 |
| WO | WO/02/100401 | 12/2002 |
| WO | WO/03/051900 | 6/2003 |

OTHER PUBLICATIONS

Barnes et al. Nuclear Factor kB—A Pivotal Transcription Factor in Chronic INflammatory Diseases, New England Journal of Medicine, Apr. 10, 1997, vol. 335, No. 15 pp. 1066-1071.*

Tu Caixia et al., A Study on the Pharmacoogical Activities of Four Kinds of Di-Indole Compounds and Exploration of its Clinical Significance, Zhonghua Pifuke Zazhi, 1991, vol. 24, No. 4, pp. 245-247, 287 see reference and translation.*

Watanabe, T. et al., "Artherosclerosis and inflammation mononuclear cell recruitment and adhesion molecules with reference to the implication of ICAM-1/LFA-1 pathway in atherogenesis", Int J Cardiol, 66 Suppl 1:S45-53; discussion S55 (1998).

Weinberg, J. et al., "Biologic Therapy for Psoriasis—The First Wave: Infliximab, Etanercept, Efalizumab, and Alefacept", J. Drugs Dermatol, 3:303-310 (2002).

Weisman, M. H., "What are the risks of biologic therapy in rheumatoid arthritis? An update on safety", J. Rheumatol Suppl., 65:33-38 (2002).

Whalen, J. D. et al., "Adenoviral transfer of the viral IL-10 gene periarticularly to mouse paws suppresses development of collagen-induced arthritis in both injected and uninjected paws", J Immunol, 162:3625-3632 (1999).

Wicki, A. et al., "The Rho/Rho-kinase and the phosphatidylinositol 3-kinase pathways are essential for spontaneous locomotion of Walker 256 carcinosarcoma cells," Int J Cancer, vol. 91, No. 6, pp. 763-771 (2001).

Williams, J. D. and Griffiths, C. E., "Cytokine blocking agents in dermatology", Clin Exp Dermatol, 27:585-590 (2002).

Written Opinion of the International Search Authority for PCT/US05/00169 dated Jul. 19, 2005.

Wu-Wong, J. R., et al., "Identification and characterization of A-105972, an antineoplastic agent," Cancer Res, vol. 61, No. 4, pp. 1486-1492 (2001).

Yamaura, T., et al., "Model for mediastinal lymph node metastasis produced by orthotopic intrapulmonary implantation of lung cancer cells in mice," Hum Cell, vol. 12, No. 4, pp. 197-204 (1999).

Yoon, J. W. et al., Cellular and molecular mechanisms for the initiation and progression of beta cell destruction resulting from the collaboration between macrophages and T cells, Autoimmunity, 27:109-122 (1998).

Yoza, B. K. et al., "Protein-tyrosine kinase activation is required for lipopolysaccharide inducution of interleukin 1beta and NFkappaB activation, but not NFkappaB nuclear translocation", J Biol Chem, 271:18306-18309 (1996).

Zhang, H. et al., "Advances in Experimental Studies on Treatment of Psoriasis by Traditional Chinese Medicine", J Tradit Chin Med, 22(1):61-66 (Mar. 2002) (Abstract only).

European Search Report for European Application No. 02805123 dated Nov. 16, 2007.

Wahl et al., "Syntheses dans le groupe des indigoides (II). Nouvelles syntheses de l'ecarlate thioindigo et de l'indirubine Asyntheses in the indigoid group. II. New syntheses of scarlet thioindigo andindirubinU", Bulletin De La Societe Chimique De France, Memoires, Masson, Paris, France, (1914) pp. 336-342—English Translation of p. 339, paragraph 4.

Wahl et al., "Chimie Organique.—un nouvel isomere de l'indigo", Comptes Rendus Hebdomadaires Des Seances De L'Academie Des Sciences, Gauthier-Villars, Paris, France, vol. 148, (1909) pp. 714-720—English Translation of p. 718, paragraph 1.

Stolle et al., "N-Substituted oxindoles and isatins", Journal Fuer Praktische Chemie (Leipzig), vol. 128, pp. 1-43—English Translation of p. 34, Example 2.

International Search Report for PCT/US2002/039866 dated Mar. 19, 2003.

International Preliminary Examination Report for PCT/US2002/039866 dated May 13, 2004.

U.S. Appl. No. 60/407,267 entitled "Derivative of Isoindigo, Indigo and Indirubin for the Treatment of Cancer" filed Sep. 3, 2002.

Stolle et al., "N-Substituted oxindoles and isatins", Journal Fuer Praktische Chemie (Leipzig), vol. 128, pp. 1-43—English Translation of p. 34, Example 2 (1930).

Isatis tinctoria, Alternative Medicine Review, 7(6):523-524 (2002).

Drug Facts and Comparisons, Wolters Kluwer Co., pp. 1210-1213 (1994).

European Office Action for European Application No. 05704992.6 dated Mar. 4, 2009 (5 sheets).

Alessi, D. R., et al., "PD 098059 is a specific inhibitor of the activation of mitogen-activated protein kinase kinase in vitro and in vivo," *J Biol Chem*, vol. 270, No. 46, pp. 27489-27494 (1995).

Andreakos, E.T. et al., "Cytokines and anti-cytokine biologicals in autoimmunity: present and future", *Cytokine Growth Factor Rev*, 13:299-313 (2002).

Antoni, C. et al., "Side effects of anti-TNF therapy: current knowledge", *Clin Exp Rheumatol*, 20:S152-157 (2002).

Autschbach, F. et al., "In situ expression of interleukin-10 in noninflamed human gut and in inflammatory bowel disease", *Am J Pathol*, 153:121-130 (1998).

Baugh et al., "Mechanisms for modulating TNFα in immune and inflammatory disease", *Curr Opin Drug Discov Devel*, 4(5):635-650 (2001).

Beagley et al., "Cells and cytokines in mucosal immunity and inflammation", *Gastroenterol Clin North Am*, 21(2):347-366 (Jun. 1992) (Abstract only).

Bebo, B. F., Jr. et al., "Hypothesis: a possible role for mast cells and their inflammatory mediators in the pathogenesis of autoimmune encephalomyelitis", *J Neurosci Res*, 45:340-348 (1996).

Bessis, N. et al., "Gene therapy for rheumatoid arthritis", *J Gene Med*, 4:581-591 (2002).

Boehrer, S., et al., "In lymphatic cells par-4 sensitizes to apoptosis by down-regulating bcl-2 and promoting disruption of mitochondrial membrane potential and caspase activation," *Cancer Res*, vol. 62, No. 6, pp. 1768-1775 (2002).

Bresnihan, B. et al., "Treatment of rheumatoid arthritis with recombinant human interleukin-1 receptor antagonist", *Arthritis Rheum*, 41:2196-2204 (1998).

Brown, S. L. et al., "Tumor necrosis factor antagonist therapy and lymphoma development: twenty-six cases reported to the Food and Drug Administration", *Arthritis Rheum*, 46:3151-3158 (2002).

Brynskov, J. et al., "Increased concentrations of interleukin 1 beta, interleukin-2, and soluble interleukin-2 receptors in endoscopical mucosal biopsy specimens with active inflammatory bowel disease", *Gut*, 33:55-58 (1992).

Buchdunger, E. et al., "Bcr-Abl inhibition as a modality of CML therapeutic,". *Biochim Biophys Acta*, vol. 1551, No. 1, pp. M11-18 (2001).

Buolamwini, J.K., "Cell Cycle Molecular Targets in Novel Anticancer Drug Discovery," *Curr. Pharm. Design*, vol. 6, pp. 379-392 (2000).

Campion, G. V. et al., "Dose-range and dose-frequency study of recombinant human interleukin-1 receptor antagonist in patients with rheumatoid arthritis. The IL-1Ra Arthritis Study Group", *Arthritis Rheum*, 39:1092-1101 (1996).

Cather et al., "Modulating T cell responses for the treatment of psoriasis: a focus on efalizumab", *Expert Opin Biol Ther*, 3:361-370 (Apr. 2003) (Abstract only).

Cooper, J.C. et al., "Alefacept selectively promotes NK cell-mediated deletion of CD45R0+ human T cells", *Eur J Immunol*, 33:666-675 (2003).

Damiens, E. et al., "Anti-mitotic properties of indirubin-3'-monoxime, a CDK/GSK-3 inhibitor: induction of endoreplication following prophase arrest," *Oncogene*, vol. 20, No. 29, pp. 3786-3797 (2001).

Dayer, J. M, "The pivotal role of interleukin-1 in the clinical manifestations of rheumatoid arthritis", *Rheumatology* (Oxford), 42 Suppl 2:ii3-10 (2003).

de Jong, B. A., et al., "Production of IL-1beta and IL-1Ra as risk factors for susceptibility and progression of relapse-onset multiple sclerosis", *J. Neuroimmunol*, 126:172-179 (2002).

Dean, J. L. et al., "The 3' untranslated region of tumor necrosis factor alpha mRNA is a target of the mRNA-stabilizing factor HuR", *Mol Cell Biol*, 21:721-730 (2001).

DeGraba, T. J., "The role of inflammation in artherosclerosis", *Adv Neurol*, 92:29-42 (2003).

Detmar, M. et al., "Overexpression of vascular permeability factor/vascular endothelial growth factor and its receptors in psoriasis", *J Exp Med*, 180:1141-1146 (1994).

Diab et al., "High IL-6 and low IL-10 in the central nervous system are associated with protracted relapsing EAE in DA rats", *J Neuropathol Exp Neurol*, 56(6):641-650 (Jun. 1997) (Abstract only).

Dickson D. W. et al., "Microglia and cytokines in neurological disease, with special references to AIDS and Alzheimer's disease", *Glia*, 7:75-83 (1993).

DiPaola, R.S. et al., "Clinical and biologic activity of an estrogenic herbal combination (PC-SPES) in prostate cancer," *N Engl J Med*, vol. 339, No. 12, pp. 785-791 (1998).

Druker, B.J. et al., "Activity of a specific inhibitor of the BCR-ABL tyrosine kinase in the blast crisis of chronic myeloid leukemia and acute lymphoblastic leukemia with the Philadelphia chromosome," *N Engl J Med*, vol. 344, No. 14, pp. 1038-1042 (2001).

Dustin, M. L. et al., "Induction by IL 1 and interferon-gamma: tissue distribution, biochemistry, and function of a natural adherence molecule (ICAM-1)", *J Immunol*,37:245-254 (1986).

Elliott, M. J. et al., "Repeated therapy with monoclonal antibody to tumour necrosis factor alpha (cA2) in patients with rheumatoid arthritis", *Lancet*, 344:1125-1127 (1994).

Fassas, A. and Kimiskidis, V. K., "Stem cell transplantation for multiple sclerosis: What is the evidence?", *Blood Rev*, 17:233-240 (2003).

Feldmann, M., "Pathogenesis of arthritis: recent research progress", *Nat Immunol*, 2:771-773 (2001).

Franceschi, C. et al., "Inflamm-aging. An Evolutionary Perspective on Immunosenescence", *Ann N Y Acad Sci*, 908:244-254 (2000).

Freitas, J.J. et al., "Walker-256 tumor growth causes oxidative stress in rat brain," *J Neurochem*, vol. 77, No. 2, pp. 655-663 (2001).

Frey, R. S. et al., "Effects of genistein on cell proliferation and cell cycle arrest in nonneoplastic human mammary epithelial cells: involvement of Cdc2, p21](waf/cip1), p27(kip1), and Cdc25C expression," *Biochem Pharmacol*, vol. 61, No. 8, pp. 979-989 (2001).

Furlan, R. et al., "Gene therapy-mediated modulation of immune processes in the central nervous system", *Curr Pharm Des*, 9:2002-2008 (2003).

Furukawa, Y., "Cell cycle control genes and hematopoietic cell differentiation," *Leuk Lymphoma*, vol. 43, No. 2, pp. 225-231 (2002).

Gabay, C., "IL-1 trap. Regeneron/Novartis", *Curr Opin Investig Drugs*, 4(5):593-597 (May 2003) (Abstract only).

Ghezzi et al., "Tumor necrosis factor and motoneuronal degeneration: an open problem", *Neuroimmunomodulation*, 9(4):178-182 (2001) (Abstract only).

Gianni, L. et al., "Nonlinear pharmacokinetics and metabolism of paclitaxel and its pharmacokinetic/pharmacodynamic relationships in humans," *J Clin Oncol*, vol. 13, No. 1, pp. 180-190 (1995).

Girolomoni et al., "Targeting tumor necrosis factor-alpha as a potential therapy in inflammatory skin diseases", *Curr Opin Investig Drugs*, 3(11):1590-1595 (Nov. 2002) (Abstract only).

Glabinski, A. et al., "Chemokine upregulation follows cytokine expression in chronic relapsing experimental autoimmune encephalomyelitis", *Scand J Immunol*, 58:81-88 (2003).

Gray, N. et al., "ATP-site Directed Inhibitors of Cyclin-dependent Kinases," *Curr. Medicinal Chem.*, vol. 6, No. 9, pp. 859-875 (1999).

Grossman, R. M. et al., "Interleukin 6 is expressed in high levels in psoriatic skin and stimulates proliferation of cultured human keratinocytes", *Proc Natl Acad Sci USA*, 86:6367-6371 (1989).

Group, C., "Phase I Clinical Trial on Meisoindigo in the Treatment of Chronic Myelogenous Leukemia", *J. Chinese Hematology*, 18:69-72 (1997) (Abstract only).

Guha, M. et al., "Lipopolysaccharide activation of the MEK-ERK ½ pathway in human monocytic cells mediates tissue factor and tumor necrosis factor alpha expression by inducing Elk-1 phosphorylation and Egr-1 expression", *Blood*, 98:1429-1439 (2001).

Guha, M. et al., "LPS induction of gene expression in human monocytes", *Cell Signal*, 13:85-94 (2001).

Haboubi, N. Y et al., "Radiation colitis is another mimic of chronic inflammatory bowel disease", *J Clin Pathol*, 45:272 (1992).

Han, J., "Traditional Chinese medicine and the search for new antineoplastic drugs,". *J Ethanopharmacol*, vol. 24, No. 1, pp. 1-17 (1988).

Haugeberg, G. et al., "Effects of rheumatoid arthritis on bone", *Curr Opin Rheumatol*, 15:469-475 (2003).

Haversen, L. et al., "Lactoferrin down-regulates the LPS-induced cytokine production in monocytic cells via NF-kappa B", *Cell Immunol*, 220:83-95 (2002).

Hochberg, M.C. et al., "Comparison of the efficacy of the tumour necrosis factor alpha blocking agents adalimumab, entanercept, and infliximab when added to methotrexate in patients with active rheumatoid arthritis", *Ann Rheum Dis*, 62 Suppl 2:ii3-ii16 (2003).

Hoessel, R. et al., "Indirubin, the active constituent of a Chinese Antileukaemia medicine, inhibits cyclin-dependent kinases," Macmillan Magazines Ltd., *Nature Cell Biology*, vol. 1, pp. 60-67 (1999).

Hotamisligil, G. S. et al., "Adipose expression of tumor necrosis factor-alpha: direct role in obesity-linked insulin resistance", *Science*, 259:87-91 (1993).

Hotamisligil, G. S. et al., "Tumor necrosis factor alpha inhibits signaling from the insulin receptor", *Proc Natl Acad Sci USA*, 91:4854-4858 (1994).

Hotamisligil, G.S. and Spiegelman, B. M., "Tumor necrosis factor alpha: a key component of the obesity-diabetes link", *Diabetes*, 43:1271-1278 (1994).

Huizing, M.T. et al., "Pharmacokinetics of paclitaxel and metabolites in a randomized comparative study in platinum-pretreated ovarian cancer patients,"*J Clin Oncol*, vol. 11, No. 11, pp. 2127-2135 (1993).

Indaram, A. V. et al., "Elevated basal intestinal mucosal cytokine levels in asymptomatic first-degree relatives of patients with Crohn's disease", *World J Gastroenterol*, 6:49-52 (2000).

Indaram, A. V. et al., "Mucosal cytokine production in radiation-induced proctosigmoiditis compared with inflammatory bowel disease", *Am J Gastroenterol*, 95:1221-1225 (2000).

International Search Report for PCT/US05/00169 dated Jul. 19, 2005.

Isaacs, K. L. et al., "Cytokine messenger RNA profiles in inflammatory bowel disease mucosa detected by polymerase chain reaction amplification", *Gastroenterology*, 103:1587-1595 (1992).

Ishihara, K. et al., "IL-6 in autoimmune disease and chronic inflammatory proliferative disease", *Cytokine Growth Factor Rev*, 13:357-368 (2002).

Ito, Hiroaki, "IL-6 and Crohn's Disease", *Current Drug Targets—Inflammation & Allergy*, 2:125-130 (2003).

Ito, T. et al., "Inflammatory Cytokines and Cardiovascular Disease", *Current Drug Targets—Inflammation & Allergy*, 2:257-265 (2003).

Ji, X.J. et al., "Pharmacological studies of meisoindigo: absorption and mechanism of action," *Biomed Environ Sci*, vol. 4, No. 3, pp. 332-337 (1991).

Jun, H. S. et al., "Absolute requirement of macrophages for the development and activation of beta-cell cytotoxic CD8+T-cells in T-cell receptor transgenic NOD mice", *Diabetes*, 48:34-42 (1999).

Kong, M. et al., "Cyclin F regulates the nuclear localization of cyclin B1 through a cyclin-cyclin interaction", *Embo J*, 19:1378-1388 (2000).

Koo, J. et al., "Traditional Chinese Medicine for the Treatment of Dermatologic Disorders", *Arch Dermatol.*, 134:1388-1393 (Nov. 1998).

Koo, J. et al., "Traditional Chinese Medicine in Dermatology", *Dermatologic Therapy*,16(2):98-105 (2003).

Kreis, W. et al., "Unique synergism or antagonism of combinations of chemotherapeutic and hormonal agents in human prostate cancer cell lines," *Br J Urol*, vol. 79, No. 2, pp. 196-202 (1997).

Kunikata et al., "Indirubin inhibits inflammatory reactions on delayed-type hypersensitivity", *European Journal of Pharmacology*, 410:93-100 (2000).

Lahiri, D.K., et al., "Role of Cytokines in the Gene Expression of Amyloid β-protein Precursor: Identification of a 5'-UTR-Binding Nuclear factor and Its Implications in Alzheimer's Disease", *Journal of Alzheimer's Disease*, 5:81-90 (2003).

Laliberte, R. E. et al., "Glutathione s-transferase omega 1-1 is a target of cytokine release inhibitory drugs and may be responsible for their effect on interleukin-1beta postranslational processing",*J. Biol Chem.*, 278:16567-16578 (2003).

Lang, C. H. et al., "Tumor necrosis factor impairs insulin action on peripheral glucose disposal and hepatic glucose output", *Endocrinology*, 130:43-52 (1992).

Lechman, E. R. et al., "Direct adenoviral gene transfer of viral IL-10 to rabbit knees with experimental arthritis ameliorates disease in both injected and contralateral control knees", *J Immunol*, 163:2202-2208 (1999).

Leclerc et al., "Indirubins Inhibit Glycogen Synthase Kinase-3β and DCK5/P25, Two Protein Kinases Involved in Abnormal Tau Phosphorylation in Alzheimer's Disease", *J. Biol. Chem.*, vol. 276, No. 1, pp. 251-260 (2001).

Li, C. et al., "The Synthesis, Antileukemic Activity, and Crystal Structures of Indirubin Derivatives," *Bull. Chem. Soc. Jpn.*, vol. 69, pp. 1621-1627 (1996).

Li, X.K. et al., "Huanglian, A chinese herbal extract, inhibits cell growth by suppressing the expression of cyclin B1 and inhibiting CDC2 kinase in human cancer cells," *Mol Pharmacol*, vol. 58, No. 6, pp. 1287-1293 (2000).

Li, Y. J. et al., "Glutathione S-Transferase Omega 1 modifies age-at-onset of Alzheimer Disease and Parkinson Disease", *Human Mol Genet* 12:3259-3267 (2003).

Lichtiger, S. et al., "Cyclosporine in Severe Ulcerative Colitis Refractory to Steroid Therapy", *New England Journal of Medicine*, 330(26):1841-1845 (Jun. 30, 1994).

Lin et al., "Meisoindigo for Psoriasis Treatment", *Chinese Journal of Dermatology*, 22(1):29-30 (1989).

Lindsberg, P. J. et al., "Inflammation and infections as risk factors for ischemic stroke", *Stroke*, 34:2518-2532 (2003).

Liu, J. H. et al., "Functional association of TGF-beta receptor II with cyclin B", *Oncogene*, 18:269-275 (1999).

Liu, X.M. et al., "Induction of differentiation and down-regulation of c-myb gene expression in ML-1 human myeloblastic leukemia cells by the clinically effective anti-leukemia agent meisoindigo," *Biochem Pharmacol*, vol. 51, No. 11, pp. 1545-1551 (1996).

Maccarrone, M. et al., "Endocannabinoid Degradation, Endotoxic Shock and Inflammation", *Current Drug Targets—Inflammation & Allergy*, 1:53-63 (2002).

MacDermott, R. P., "Alterations in the mucosal immune system in ulcerative colitis and Crohn's disease", *Med Clin North Am*, 78:1207-1231 (1994).

Marko, D. et al., "Inhibition of cyclin-dependent kinase 1 (CDK1) by indirubin derivatives in human tumour cells," *Br J Cancer*, vol. 84. No. 2, pp. 283-289 (2001).

Matsuura, T. et al., "Immune activation genes in inflammatory bowel disease", *Gastroenterology*, 104:448-458 (1993).

McGeer, E. G. et al., "Inflammatory processes in Alzheimer's disease", *Prog Neuropsychopharmacol Biol Psychiatry*, 27:741-749 (2003).

McGovern, S. L. et al., "Kinase inhibitors: not just for kinases anymore", *J Med Chem*, 46:1478-1483 (2003).

Mendonca, C. O. et al., "Current concepts in psoriasis and its treatment", *Pharmacol Ther*, 99:133-147 (2003).

Mennicken, F. et al., "Chemokines and chemokine receptors in the CNS: a possible role in neuroinflammation and patterning", *Trends Pharmacol Sci*, 20:73-78 (1999).

Merck Manual of Diagnosis and Therapy, 15th Edition, pp. 1218-1219 (1987).

Mitani, N. et al., "Inhibitory effect of berberine on the mediastinal lymph node metastasis produced by orthotopic implantation of Lewis lung carcinoma," *Cancer Lett*, vol. 165, No. 1, pp. 35-42 (2001).

Moreland, L. W. et al., "Treatment of rheumatoid arthritis with a recombinant human tumor necrosis factor receptor (p75)-Fc fusion protein", *N Engl J Med*, 337:141-147 (1997).

Morgan, D.O., "Principles of CDK regulation," *Nature*, vol. 374, No. 6518, pp. 131-134 (1995).

Murthy, S. et al., "The Efficacy of BAY y 1015 in Dextran Sulfate Model of Mouse Colitis", *Inflamm. Res.*, 46:224-233 (1997).

Murthy, S. et al., "Treatment of Dextran Sulfate Sodium-Induced Murine Colitis by Intracolonic Cyclosporin", *Digestive Disease and Sciences*, 38(9):1722-1734 (Sep. 1993).

Najarian, D. J. et al., "Connections between psoriasis and Crohn's disease", *J Am Acad Dermatol*, 48:805-821; quiz 822-824 (2003).

Noguchi, M. et al., "Secretion imbalance between tumour necrosis factor and its inhibitor in inflammatory bowel disease", *Gut*, 43:203-209 (1998).

Ofei, F. et al., "Effects of an engineered human anti-TNF-alpha antibody (CDP571) on insulin sensitivity and glycemic control in patients with NIDDM", *Diabetes*, 45:881-885 (1996).

Ohtsu, T. et al., "Clinical pharmacokinetics and pharmacodynamics of paclitaxel: a 3-hour infusion versus a 24-hour infusion," *Clin Cancer Res*, vol. 1, No. 6, pp. 599-606 (1995).

Okayasu, I. et al., "A novel method in the induction of reliable experimental acute and chronic ulcerative colitis in mice", *Gastroenterology*, 98:694-702 (1990).

Osman, F. et al., "A cis-acting element in the 3'-untranslated region of human TNF-alpha mRNA renders splicing dependent on the activation of protein kinase PKR", *Genes Dev*, 13:3280-3293 (1999).

Palladino, M. A. et al., "Anti-TNF-alpha therapies: the next generation", *Nat Rev Drug Discov*, 2:736-746 (2003).

Rabinovitch, A. et al., "Role of cytokines in the pathogenesis of autoimmune diabetes mellitus", *Rev Endocr Metab Disord*, 4:291-299 (2003).

Robertson, J. et al., "Apoptotic death of neurons exhibiting peripherin aggregates is mediated by the proinflammatory cytokine tumor necrosis factor-alpha", *J Cell Biol*, 155:217-226 (2001).

Rogers, J. et al., "A Perspective on Inflammation in Alzheimer's Disease", *Ann N Y Acad Sci*, 924:132-135 (2000).

Ruan, H. et al., "Insulin resistance in adipose tissue: direct and indirect effects of tumor necrosis factor-alpha", *Cytokine Growth Factor Rev*, 14:447-455 (2003).

Ruan, H. et al., "Troglitazone antagonizes tumor necrosis factor-alpha-induced reprogramming of adipocyte gene expression by inhibiting the transcriptional regulatory functions of NF-kappaB", *J Biol Chem*, 278:28181-28192 (2003).

Rutgeerts, P. et al., "Treatment of active Crohn's disease with onercept (recombinant human soluble p55 tumour necrosis factor receptor): results of a randomized, open-label, pilot study", *Ailment Pharmacol Ther*, 17:185-192 (2003).

Rutgeerts, P., "A critical assessment of new therapies in inflammaotry bowel disease", *J Gastroenterol Hepatol*, 17 Suppl:S176-185 (2002).

Samoilova, E. B. et al., "IL-6-deficient mice are resistant to experimental autoimmune encephalomyelitis: roles of IL-6 in the activation and differentiation of autoreactive T cells", *J Immunol*, 161:6480-6486 (1998).

Schmidt, M. I. and Duncan, B. B., "Diabesity: an inflammatory metabolic condition", *Clin Chem Lab Med*, 41:1120-1130 (2003).

Schon, M. P., "Animal models of psoriasis—what can we learn from them?", *J Invest Dermatol*, 112:405-410 (1999).

Schreiber, A. B. et al., "Transforming growth factor-alpha: a more potent angiogenic mediator than epidermal growth factor", *Science*, 232:1250-1253 (1986).

Schreiber, S. et al., "Immunoregulatory role of interleukin 10 in patients with inflammatory bowel disease", *Gastroenterology*, 108:1434-1444 (1995).

Schumann, R. R. et al., "Lipopolysaccharide activates caspapse-1 (interleukin-1-converting enzyme) in cultured monocytic and endothelial cells", *Blood*, 91:577-584 (1998).

Senderowicz, A.M., "Development of cyclin-dependent kinase modulators as novel therapeutic approaches for hematological malignancies," *Leukemia*, vol. 15, No. 1, pp. 1-9 (2001).

Sharifi, N. et al., "Targeted chemotherapy: chronic myelogenous leukemia as a model," *J Mol Med*, vol. 80, No. 4, pp. 219-232 (2002).

Sovak et al., "Herbal Composition PC-SPES for Management of Prostate Cancer: Identification of Active Principles", *Journal of the National Cancer Institute*, 94(17):1275-1281 (Sep. 4, 2002).

Steinman, R. A., "Cell cycle regulators and hematopoiesis," *Oncogene*, vol. 21, No. 21, pp. 3403-3413 (2002).

Strange, P. et al., "Interferon gamma-treated keratinocytes activate T cells in the presence of superantigens: involvement of major histocompatability complex class II molecules", *J Invest Dermatol* 102:150-154 (1994).

Subramanian, N. et al., "Interleukin 1 releases histamine from human basophils and mast cells in vitro", *J Immunol*, 138:271-275 (1987).

Sullivan, G.W. et al., "The role of inflammation in vascular diseases", *J Leukoc Biol*, 67:591-602 (2000).

Suri, A. et al., "Dissecting the role of CD4+ T cells in autoimmune diabetes through the use of TCR transgenic mice", *Immunol Rev* 169:55-65 (1999).

Tanaka, Y. et al., "Inter- and intracellular signaling in secondary osteoporosis", *J Bone Miner Metab*, 21:61-66 (2003).

Tang, X. et al., "Identification and functional characterization of a novel binding site on TNF-alpha promoter", *Proc Natl Acad Sci USA*, 100:4096-4101 (2003).

Tracy, R. P., "Inflammation, the metabolic syndrome and cardiovascular risk", *Int. J. Clin Pract*, Suppl 10-17 (Mar. 2003) (Abstract only).

Tsuchiya, S. et al., "Establishment and characterization of a human acute monocytic leukemia cell line (THP-1)", *Int J Cancer*, 26:171-176 (1980).

Uysal, K. T., et al., "Protection fom obesity-induced insulin resistance in mice lacking TNF-alpha function", *Nature*, 389:610-614 (1997).

Virdis, A. and Schiffrin, E. L., "Vasculalr inflammation: a role in vascular disease in hypertension?", *Curr Opin Nephrol Hypertens*, 12:181-187 (2003).

von der Thusen, J. H., et al., "Interleukins in atherosclerosis: molecular pathways and therapeutic potential", *Pharmacol Rev*, 55:133-166 (2003).

Wang, E. et al., "Posttranscriptional regulation of protein expression in human epithelial carcinoma cells by adenine-uridine-rich elements in the 3'-untranslated region of tumor necross factor-alpha messenger RNA", *Cancer Res*, 57:5426-5433 (1997).

Wang, L.G., et al., "Activation of casein kinase II in ML-1 human myeloblastic leukemia cells requires IGF-1 and transferrin," *J Leukoc Biol*, vol. 57, No. 2, pp. 332-334 (1995).

Wang, L. G. et al., "Down-regulation of prostate-specific antigen expression by finasteride through inhibition of complex formation between androgen receptor and steroid receptor-binding consensus in the promoter of the PSA gene in LNCaP cells", *Cancer Res*, 57:714-719 (1997).

* cited by examiner ns of US 7,855,223 B2

METHOD OF TREATING INFLAMMATORY ARTHRITIS

CROSS-REFERENCE TO RELATED APPLICATIONS

This application is a continuation-in-part of U.S. patent application Ser. No. 10/754,547, filed Jan. 12, 2004, now abandoned the content of which is expressly incorporated herein by reference thereto.

TECHNICAL FIELD

The present invention is directed to a method for treating inflammatory arthritis in a mammal. The method comprises administering to a mammal a therapeutically effective amount of at least one compound selected from indigo, isoindigo, indirubin or derivatives thereof, such as Meisoindigo (NATURA-α) or NATURA. The present invention is further directed to pharmaceutical compositions that include at least one compound of the invention, an anti-inflammatory arthritis agent and a pharmaceutically acceptable carrier.

BACKGROUND OF THE INVENTION

Inflammatory arthritis is a musculoskeletal disorder and the leading cause of disability in the United States. Forty million Americans, representing 15% of the population, have some form of arthritis, and that figure is expected to increase to 59.4 million (18.2%) by the year 2020, an increase of 57% in the number of persons affected. Arthritis patients make more than 315 million physician visits and are hospitalized more than 8 million times a year. Arthritis costs the nation more than $65 billion annually in medical costs and lost productivity. Osteoarthritis (OA), or degenerative joint disease, is the most common type of arthritis, affecting 20.7 million people, (12.1%) of U.S. adults in 1990, now estimated at 37 million, and trailed chronic heart disease as the leading cause of Social Security payments due to long-term absence from work. (Lawrence, Helmick et al. 1998).

Approximately 1-2% of the population suffers from rheumatoid arthritis (RA), which is characterized as an imbalance in the immune system that causes an overproduction of pro-inflammatory cytokines, e.g., tumor necrosis factor alpha (TNF-α, interleukin 1 (IL-1), and a lack of anti-inflammatory cytokines, e.g. IL-10, IL-11. RA is characterized by synovial inflammation, which progresses to cartilage destruction, bone erosion and subsequent joint deformity. The primary symptoms of RA are joint inflammation, swelling, difficulty moving, and pain. During the inflammatory process, polymorphonuclear cells, macrophages, and lymphocytes are released. Activated T-lymphocytes produce cytotoxins and pro-inflammatory cytokines, while macrophages stimulate the release of prostaglandins and cytotoxins. Vasoactive substances (histamine, kinins, and prostaglandins) are released at the site of inflammation and cause edema, warmth, erythema, and pain associated with inflamed joints. In the late stage of RA, enzymes produced by the inflamed cells may digest bone and cartilage. The long-term damage results in chronic pain, loss of function, deformity, disability in the joints and even a shortened life expectancy. The prevalence of RA around world is constantly at 0.5-1.0% of total population, with exceptions in the Pima Indians and the Chippewa Indians at higher rates of 5.3% and 6.8%, respectively, and in Chinese and Japanese reportedly at lower rates (Silman and Pearson 2002).

Osteoarthritis usually presents as pain, which worsens with exercise or simply an X-ray that clearly shows thinning cartilage. Common joints affected are the knees, hips and spine, finger, base of thumb and base of the big toe. Osteoarthritis is characterized by degenerative changes in the articular cartilage and subsequent new bone formation at the articular margins. The primary defect in hyaline cartilage, at the articular surface of the joint, is an alteration in the ratio of total glycosaminoglyeans to that of the collagen fiber content in the matrix. By age 60, almost all Americans have osteoarthritis in their necks or spines.

Current medications to treat inflammatory arthritis can be classified as analgesics; corticosteroids (e.g., glucocorticoids, or steroids); NSAIDs (non-steroidal anti-inflammatory drugs); DMARDS (disease-modifying anti-rheumatic drugs), and biologic DMARDS.

Controlling pain is a vital part of treating arthritis. Analgesics can only provide a temporary pain relief. They neither reduce inflammation nor slow progression of the disease. Acetaminophen (Tylenol) is the most commonly used analgesic. Narcotic analgesic drugs can also be prescribed for more severe pain.

Corticosteroids are closely related to cortisol, a hormone produced on the cortex of the adrenal glands. Treatment of rheumatoid arthritis with corticosteroids remains controversial in terms of benefit/harm trade-offs (Boers 2004). Corticosteroids are considered as very potent drugs because of their ability to reduce swelling and inflammation rapidly. However, it is well known that corticosteroids can potentially cause serious and permanent side effects. Therefore, they may only be used in certain situations systemically or locally into a specific joint for relief, always at the lowest possible effective dose for the shortest possible duration with gradually weaning off or tapering the dose over time.

NSAIDs are distinguished from coticosteroids. NSAIDs at low doses reduce pain, and at higher doses relieve inflammation. Most NSAIDs are inhibitors of the enzyme cyclooxygenase, inhibiting non-selectively both the cyclooxygenase-1 (COX-1) and cyclooxygenase-2 (COX-2). Cyclooxygenase is the rate-limiting enzyme in catalyzing the formation of prostaglan prostaglandins and thromboxane from arachidonic acid. Prostaglandins among others function as messenger molecules in the process of inflammation. COX-1 is an enzyme constitutively expressed with a "house-keeping" role in regulating many normal physiological processes. The adverse effects of NSAIDs are mainly related to their inhibition of COX-1 in kidney and gastrointestinal tracts where prostaglandins serve a protective role. COX-2 is an enzyme with low or non-detectable expression in most tissues, but can be readily induced in response to cell activation by cytokines, growth factors and tumor promoters. Therapeutic effects of NSAIDs are due to their inhibition on COX-2. While selective COX-2 inhibitors, Coxibs (celecoxib, rofecoxib, valdecoxib, parecoxib and etoricoxib), were thought to have anti-inflammatory action without disrupting gastroprotective prostaglandins, an increased cardiovascular risk was seen in clinical applications which resulted in the worldwide withdrawal of some Coxibs (rofecoxib and Valdecoxib) (Caporali and Montecucco 2005).

While the NSAID reduces day-to-day inflammation, stronger medicines, DMARDs, are usually required for patients with persistent inflammation in several joints due to inflammatory arthritis for longer than six weeks. The DMARDs slow down the biological processes that are the driving force behind persistent inflammation. DMARDs are slow-acting anti-rheumatic drugs. The quickest-acting DMARD is methotrexate, which usually takes four to six weeks before seeing benefits. The rest of the DMARDs can take three to six months or even longer to be effective. As DMARDs suppress the immune system, serious adverse effects may occur over long-term use. Methotrexate has emerged as an effective treatment for RA either as a single agent or in combination with other DMARDs (Borchers, Keen et al. 2004). The toxicity profile of methotrexate is well established and includes serious and sometimes fatal liver disease, pneumonitis, and cytopenias.

The most exciting progress in recent years in the treatment of RA is the development of biologic DMARDs (Klippel 2000). Elucidation of the key role of TNF-α in the pathogenesis of RA has led to the development of targeted therapeutics blocking the activity of this cytokine. In addition to anti-TNF therapy, a number of other biologic DMARDs have been developed specifically against molecules (IL-1) or cells (B cells and T cells) involved in the process of immune-related diseases. Potential advantages of biologic DMARDs over traditional DMARDs, include highly specific blockage of the target molecules critically involved in the pathogenesis, rapid onset of clinical action, minimized nonspecific toxicity, long dosing intervals (every other week subcutaneously or every other month intravenously), possible long-term immunomodulatory effects, and improved quality of life. Biological DMARDs used for arthritis include those blocking inflammatory cytokines (Maini and Taylor 2000), specifically depleting B cells (Higashida, Wun et al. 2005) and selectively inhibiting activation of T cells (Kremer et al, 2005).

Since biological DMARDs have only recently been in clinical use, their long term efficacy and adverse effects remain to be evaluated. In theory, strong and specific blockage or depletion of molecules or cells that are critically involved in normal physiological process will inevitably result in undesirable consequence (Mencher and Wang 2005). In deed, serious infections and tumors have been observed in trials with small cohorts of patients taking anti-TNF therapy (Askling, Fored et al. 2005; Chakravarty, Michaud et al. 2005; Listing, Strangfeld et al. 2005). A collective of randomized, placebo-controlled trials of the anti-TNF antibodies (infliximab and adalimumab) used for 12 weeks or more in patients with rheumatoid arthritis indicates that anti-TNF-treated patients (3493 patients) compared with placebo patients (1512 patients) have significant increase in incidence of serious infections (relative risk: 2.0) and malignancies (relative risk: 3.3)(Bongartz, Sutton et al. 2006).

All these biological DMARDs are either recombinant proteins or antibodies. They are very expensive. Yearly cost for a patient typically exceeds $12,000. The cost of biological DMARDs administrated by injection or perfusion is the major drawback limiting greater use (Wong 2004).

Although a wide range of drugs are available, the successful and cost effective treatment of inflammatory arthritis is still a major unmet medical need. While biologic DMARDs are offering the most promising route to slowing or even halting this disease, they are expensive and work only for a proportion of patients. Even for the most effective anti-TNF therapy, at least one third of RA patients do not respond (Navarro-Sarabia, Ariza-Ariza et al. 2006; Symmons and Silman 2006; Moreland 2005; and Reimold 2002).

SUMMARY OF THE INVENTION

The present invention is directed to a method of treating inflammatory arthritis in a cost effective manner. The method preferably includes the step of administering to an animal a therapeutically effective amount of at least one compound selected from the group consisting of: indigo, isoindigo, indirubin or derivatives thereof. Preferred derivatives include compounds of formula (I), (II) or (III)

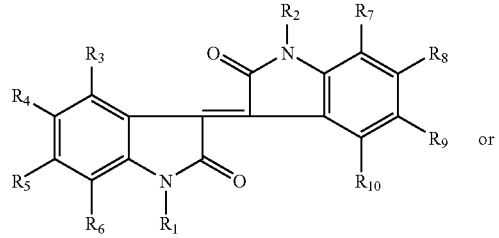

FORMULA (I)

or

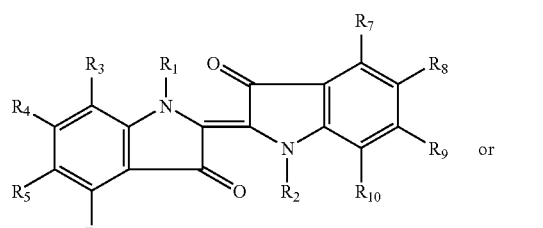

FORMULA (II)

or

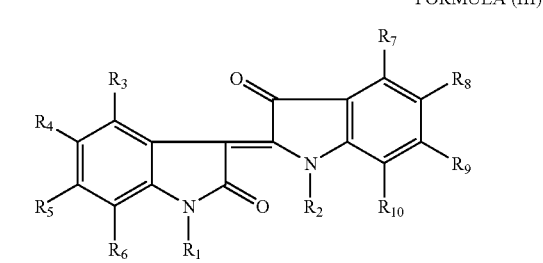

FORMULA (III)

wherein $R_3$, $R_4$, $R_5$, $R_6$, $R_7$, $R_8$, $R_9$, and $R_{10}$ are the same or different and represent a hydrogen atom; a hydroxy group; a nitroso group; a nitro group; a monosaccharide; a disaccharide; a halogen atom; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a —$R_{11}R_{12}$ group, wherein $R_{11}$ and $R_{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R_{11}$ and $R_{12}$ form together a ring having 2 to 6, optionally substituted, $CH_2$ groups; an azo group —N═N—$R_{13}$, wherein $R_{13}$ represents an aromatic system which can be substituted by one or more carboxyl groups and/or phosphoryl groups, or a group selected from the group consisting of sugars, amino acids, peptides or steroid hormones; or $R_1$ and $R_6$, and $R_2$ and $R_7$, respectively, form independently from each other a ring together having 1 to 4, optionally substituted, $CH_2$ groups; and $R_1$ and $R_2$ are the same or different and represent a hydrogen atom; a halogen atom; a hydroxy group; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; a —$NR_{17}R_{18}$ group, wherein $R_{17}$ and $R_{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —$CH_2$—$NR_{17}R_{18}$, wherein $R_{17}$ and $R_{18}$ have the above definitions; a physiological amino acid residue bound to the nitrogen as an amide, substituted or unsubstituted monosaccharide, disaccharides or oligosaccharides; or a sugar, amino acid, peptide or steroid hormone.

Specific preferred compounds include N-methyl-Δ3,3'-dihydroindole-2,2' diketone or 1-(β-D-O-triacetyl-xylopranosyl)-isoindigo.

The arthritis to be treated can be any inflammatory related arthritis. In a preferred embodiment the inflammatory arthritis is rheumatoid arthritis, ankylosing spondylitis, psoriatic arthritis, or osteoarthritis. Typically the inflammatory arthritis involves inflammation of at least one joint in the animal. The animal can be any animal, but preferably a mammal and more preferable a human.

Administration to the animal is preferably oral, mucosal (e.g., nasal, sublingual, vaginal, buccal, or rectal), parenteral (e.g., subcutaneous, intravenous, bolus injection, intramuscular, or intraarterial), or transdermal. The dosage is generally from 0.01 mg/kg/day to 150 mg/kg/day and more preferably 5-100 mg/kg/day. In one particular embodiment, the animal is a human and the amount is from 5-100 mg/day.

Preferably the compound is administered to the animal for a period of at least one week, more preferably for at least a month, and even more preferably for at least 45 days.

In a non-limiting embodiment, the compound being administered is in an amount sufficient to treat the inflammatory-related disease by inhibiting pro-inflammatory cytokine expression and/or by stimulating anti-inflammatory cytokines, but less than sufficient to substantially inhibit cyclin dependent kinases (CDKs).

Preferably the compound is administered at a concentration sufficient to inhibit at least one cytokine selected from the group consisting of: IL-1α, β, IL-2, IL-3, IL-6, IL-7, IL-9, IL-12, IL-17, IL-18, TNF-α, LT, LIF, Oncostatin or IFNc1α, β, γ. The compound preferably is also administered in an amount sufficient to stimulate expression of at least one cytokine selected from the group consisting of IL-4, IL-10, IL-11, W-13 or TGFβ. In a preferred embodiment the compound is administered in an amount sufficient to modulate cytokines TNF-α, IL-1β, IL-6, and IL-10.

Advantageously, the compound is preferably administered in an amount sufficient to modulate a humoral response in the animal being treated that result in a change in total IgG antibody in the animal. Preferably the modulation of total IgG antibody includes modulation of IgG2a, and IgG1 isotypes.

In certain embodiments, the compound is administered in an amount sufficient to cause a shift in TH1 cell response to a TH2 cell response in the animal and the compound modulates a regulatory T cell, for example, CD4+CD25+Foxp3+ cell in the spleen and/or the peripheral blood.

In one embodiment, at least two compounds selected from indigo, isoindigo, indirubin or derivatives thereof are administered concurrently or sequentially.

Advantageously, the compound is preferably administered in a pharmaceutical composition comprising at least one compound indigo, isoindigo, indirubin or derivatives thereof and a pharmaceutical carrier. Preferably, the composition would further include at least one anti-inflammatory arthritis agent selected from the group consisting of: an analgesic, a COX-2 inhibitor, a corticosteroid, non-steroidal anti-inflammatory drug (NSAID); a disease modifying anti-rheumatic drug (DMARD); and a biologic disease modifying anti-rheumatic drug (biologic DMARD). In an alternative embodiment, the anti-inflammatory arthritis agent could simply be administered in conjunction with the compound. For example, the anti-inflammatory arthritis agent could be administered by injection and the compound administered orally concurrently or sequentially.

The present invention is further directed to pharmaceutical compositions that include at least one compound selected from the group consisting of indigo, isoindigo, indirubin or derivatives thereof, for example, include N-methyl-Δ3,3'-dihydroindole-2,2' diketone (NATURA-α) or 1-(β-D-O-Triacetyl-xylopranosyl)-isoindigo (NATURA), an anti-inflammatory arthritis agent and a pharmaceutically acceptable carrier.

DETAILED DESCRIPTION OF THE PREFERRED EMBODIMENTS

Figure 1:
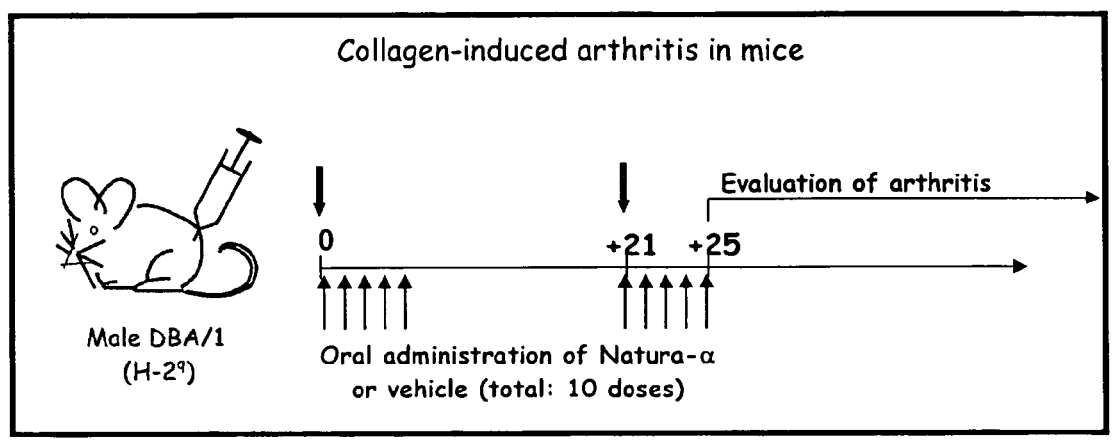
FIG. 1 shows the experimental protocol for the treatment of collagen-induced arthritis (CIA) with NATURA-α or vehicle. The experimental protocol for treatment of CIA with gavage of mice was performed twice for five consecutive days: first, at priming and second, at challenge with collagen II (CII). After the last administration of the drug, mice were dispatched in order to get two mice from each group per cage.

All patents and literature references cited in this specification are hereby incorporated by reference in their entirety. As used in the specification and in the claims, "a" can mean one or more, depending upon the context in which it is used.

The present invention is directed to methods of treating inflammatory arthritis. The method preferably includes the step of administering to an animal a therapeutically effective amount of at least one compound selected from the group consisting of: indigo, isoindigo, indirubin or derivatives thereof. Preferred derivatives include compounds of formula (I), (II) or (III)

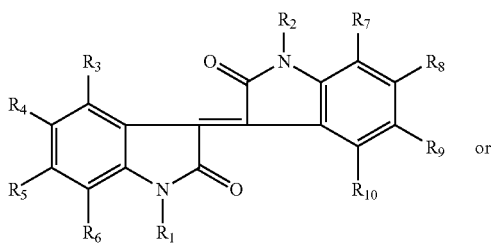

FORMULA (I)

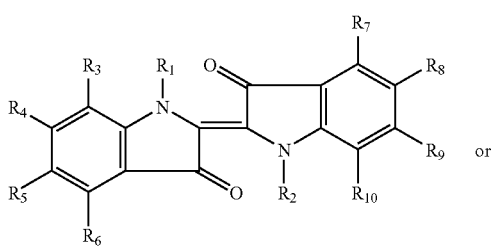

FORMULA (II)

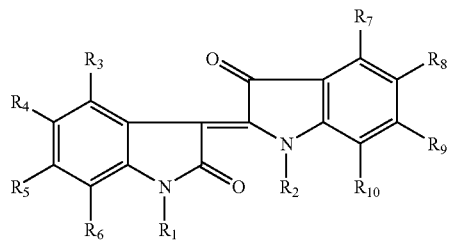

FORMULA (III)

wherein $R_3$, $R_4$, $R_5$, $R_6$, $R_7$, $R_8$, $R_9$, and $R_{10}$ are the same or different and represent a hydrogen atom; a hydroxy group; a nitroso group; a nitro group; a monosaccharide; a disaccharide; a halogen atom; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a —$R_{11}R_{12}$ group, wherein $R_{11}$ and $R_{12}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group, or $R_1$ and $R_{12}$ form together a ring having 2 to 6, optionally substituted, $CH_2$ groups; an azo group —N═N—$R_{13}$, wherein $R_{13}$ represents an aromatic system which can be substituted by one or more carboxyl groups and/or phosphoryl groups, or a group selected from the group consisting of sugars, amino acids, peptides or steroid hormones; or $R_1$ and $R_6$, and $R_2$ and $R_7$, respectively, form independently from each other a ring together having 1 to 4, optionally substituted, $CH_2$ groups; and $R_1$ and $R_2$ are the same or different and represent a hydrogen atom; a halogen atom; a hydroxy group; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms; a mono-, di- or trialkylsilyl group having 1 to 6 carbon atoms independently of each other in each instance in the straight-chain or branched-chain alkyl group; a mono-, di- or triarylsilyl group with substituted or unsubstituted aryl groups independently of each other in each instance; a —$NR_{17}R_{18}$ group, wherein $R_{17}$ and $R_{18}$ can be the same or different and represent a hydrogen atom, a straight-chain or branched-chain alkyl group having 1 to 18 carbon atoms which can additionally carry one or more hydroxy and/or amino groups, a substituted or unsubstituted aryl group which can comprise one or more heteroatoms, or an acyl group; a methyleneamino group —$CH_2$—$NR_{17}R_{18}$, wherein $R_{17}$ and $R_{18}$ have the above definitions; a physiological amino acid residue bound to the nitrogen as an amide, substituted or unsubstituted monosaccharide, disaccharides or oligosaccharides; or a sugar, amino acid, peptide or steroid hormone.

Preferred compounds are those in which at least one $R_1$, $R_2$, $R_3$, $R_4$, $R_5$, $R_6$, $R_7$, $R_8$, $R_9$, or $R_{10}$ is independently a monosaccharide, a disaccharide, or a hydrocarbyl group or a functional hydrocarbyl group substituted with one or more hydroxy moieties, carboxy moieties, nitroxy moieties, monosaccharides, disaccharides, amines, amides, thiols, or halogens, wherein the hydrocarbyl has 1 to 8 carbon atoms; and at least one of $R_1$, $R_2$, $R_3$, $R_4$, $R_5$, $R_6$, $R_7$, $R_8$, $R_9$, or $R_{10}$ enhances the bioactivity or bioavailability of the compound.

It is preferable that $R_1$, $R_2$, $R_3$, $R_4$, $R_5$, $R_6$, $R_7$, $R_8$, $R_9$, or $R_{10}$ enhances the bioactivity or bioavailability of the compound by increasing the solubility of the compound. It is more preferable that both the bioactivity and bioavailability are increased by one or more of $R_1$, $R_2$, $R_3$, $R_4$, $R_5$, $R_6$, $R_7$, $R_8$, $R_9$, or $R_{10}$.

Preferred compounds are those in which at least $R_1$ or $R_2$ is a monosaccharide; a disaccharide unsubstituted or substituted with one or more hydroxy moieties or carboxy moieties; a halogen; a hydrocarbyl group, or a functional hydrocarbyl group unsubstituted or substituted with one or more hydroxy moieties, carboxy moieties, nitroxy moieties, monosaccharides, disaccharides, amines, amides, thiols, sulfates, sulfonates, sulfonamides or halogens, wherein the hydrocarbyl has 1 to 8 carbon atoms. In many cases only one of $R_1$ or $R_2$ needs to be one of the recited moieties, with one of the most preferred substituents being —$CH_2CH_2OH$.

More preferred compounds of formulas (I), (II), and (III) are ones in which $R_1$ or $R_2$ is a methyl group or a glycoside molecule, e.g., a monosaccharide, and most preferably an acetylated monosaccharide. In a preferred embodiment the glycoside molecule is selected from an acetylated arabinose, glucose, mannose, ribose or xylose molecule.

The term "hydrocarbyl" in the context of the present invention, and in the above formulas, broadly refers to a monovalent hydrocarbon group in which the valence is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 12 carbon atoms. The preferred embodiments include those in which the hydrobcarbyl group has 1 to 8 carbon atoms. These and other hydrocarbyl groups may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionalities and/or leaving groups. Reactive functionalities refer to functionalities, which are reactive with common monomer/polymer functionalities under normal conditions well understood by those persons of ordinary skill in the relevant art. Examples of reactive functionalities are active hydrogen containing groups such as hydroxyl, amino, carboxyl, thio, amido, carbamoyl and activated methylene; isocyanato, cyano and epoxy groups; ethylenically unsaturated groups such as allyl and methallyl; and activated unsaturated groups such as acryloyl and methacryloyl, and maleate and maleimido (including the Diels-Alder adducts thereof with dienes such as butadiene). Latent reactive functionalities within the meaning of the present invention and, as would clearly be understood by those persons of ordinary skill in the relevant art, refers to reactive functionalities which are blocked or masked to prevent premature reaction. Examples of latent reactive functionalities are ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. Examples of leaving groups are halogen atoms such as chlorine, bromine and iodine; quaternary ammonium salts; sulfonium salts; and sulfonates.

A monosaccharide or disaccharide of the present invention is preferably glucose, fructose, ribulose, galactose, mannose, cellobiose, allose, altrose, ribose, xylose, arabinose, sucrose, or lactose. Most preferably it is D-glucose, D-ribose, D-galactose, D-lactose, D-xylose or D-sucrose.

In one preferred embodiment the monosaccharide or disaccharide is acetylated, preferably at least di-acetylated and more preferably tri-acetylated, e.g., tri-acetylated xylopranosyl.

The term "halogen" indicates fluorine, chlorine, bromine, or iodine. Preferably it is fluorine or chlorine.

As used herein, amino acid means an L- or D-amino acid (or a residue thereof), preferably L-, selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine. The term peptide is two or more amino acids joined by a peptide bond, preferably containing 2 to 8 amino acids, and more preferably containing 2 to 6 amino acids.

In a preferred embodiment, the compound is formula (IV), (V), or (VI):

FORMULA (IV)

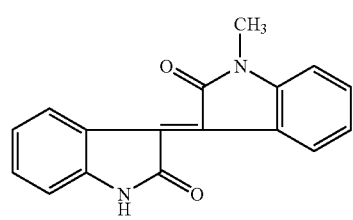

FORMULA (V)

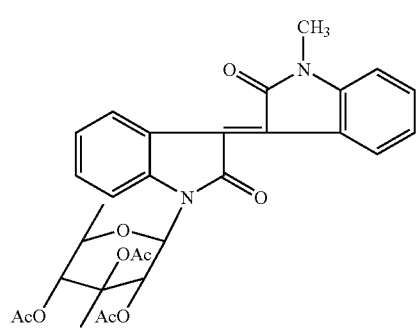

-continued

FORMULA (VI)

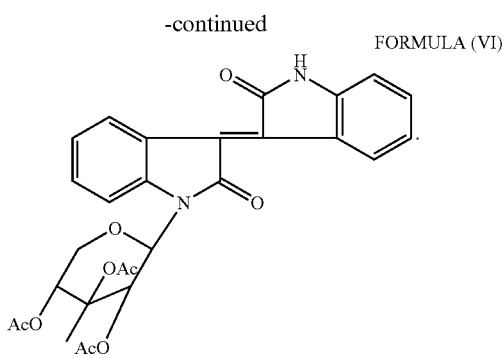

More preferably the compound is N-methyl-Δ3,3'-dihydroindole-2,2' diketone or 1-(β-D-O-triacetyl-xylopranosyl)-isoindigo.

"Inflammatory arthritis" as used in the context of the present invention refers to chronic inflammation, (regardless of the cause but typically due to an autoimmune process that affects the joints), in the tissue around the joints, such as the tendons, ligaments, and muscles, as well as other organs in the body. Preferably the inflammatory arthritis being treated is rheumatoid arthritis (RA), juvenile RA, ankylosing spondylitis, psoriatic arthritis, or osteoarthritis. A preferred therapy target is rheumatoid arthritis.

The term "treatment" in the context of the present invention refers to any improvement in the clinical symptoms of the inflammatory arthritis, as well as any improvement in the well being of the patients, in particular an improvement manifested by at least one of the following: decreased swelling and tenderness of the joints, decrease in pain in the joints, improved motility, slowing of the deterioration of the joints and the surrounding tissue, increase in the remission period between acute disease attacks; decrease in the time length of the acute attack; prevention of the onset of severe disease, etc. It should be understood that the present methods include, but is not limited to, treating inflammatory arthritis by preventing inflammation associated with arthritis. In one embodiment this is accomplished by administering an amount sufficient to regulate the cytokines involved in the pathological progress of the inflammation, thus preventing the onset arthritis.

The therapeutically "effective amount" is the amount necessary to treat the arthritis or a symptom of arthritis. The effective amount can be readily determined, in accordance with the invention, by administering to a plurality of tested subjects various amounts of the active agent and then plotting the physiological response (for example an integrated "arthritic index" combining several of the therapeutically beneficial effects) as a function of the amount. The amount above which the therapeutic beneficial effects begin to decrease (but is still lower than the MTS) is the "effective amount." Due to statistical distribution typically the "effective amount" is not a single parameter but a range of parameters.

Preferably the compound is in an amount sufficient to inhibit pro-inflammatory cytokine expression and/or to stimulate anti-inflammatory cytokine expression. In one embodiment, the compound is preferably in an amount sufficient to inhibit at least 30% expression of one or more of the pro-inflammatory cytokines selected from the group consisting of: IL-1α, β, IL-2, IL-3, IL-6, IL-7, IL-9, IL-12, IL-17, IL-18, TNF-α, LT, LIF, Oncostatin, and IFNc1α, β, γ. More preferably at least 40% expression of the cytokine is inhibited and most preferably 50% or more is inhibited. In another embodiment, the compound is preferably in an amount to stimulate anti-inflammatory cytokine expression. In this embodiment, the compound is preferably in an amount sufficient to increase the anti-inflammatory cytokine selected from the group consisting of: cytokine IL-4, IL-10, IL-11, W-13 or TGFβ by at least 25%, more preferably at least 50%, and most preferably at least 75%. Preferably the compound is administered in an amount sufficient to modulate cytokines TNF-α, IL-1β, IL-6, and IL-10.

In one non-limiting embodiment the compound is administered in an amount sufficient to modulate a humoral response in the animal being treated, preferably resulting in a change in total IgG antibody in the animal that includes changes in IgG2a, and IgG1 isotypes.

In another embodiment, the compound is in an amount sufficient to cause a shift in TH1 cell response to a TH2 cell response in the animal or sufficient to modulate regulatory T cells, preferably a CD4+CD25+Foxp3+ cell. Preferably the CD4+CD25+Foxp3+ cell is in the spleen and/or the peripheral blood.

In yet another embodiment, the invention is directed to the treatment of an animal diagnosed as having inflammatory arthritis or susceptible thereto. Preferably the animal is a mammal (e.g., a horse, cow, dog, cat, sheep, etc.) and more preferable the animal is a human. For administration to non-human animals in particular, the composition containing the therapeutic compound may be added to the animal's feed or drinking water. Also, it will be convenient to formulate animal feed and drinking water products so that the animal takes in an appropriate quantity of the compound in its diet. It will further be convenient to present the compound in a composition as a premix for addition to the feed or drinking water. The composition can also added as a food or drink supplement for humans.

It should also be noted that therapeutic benefits are typically realized by the administration of at least 1, 2, 3 or more of the compounds concurrently or sequentially. The compounds of the invention may also be combined with other therapies to provide combined therapeutically effective amounts. The compound can be administered, for example, in combination or in conjunction with additional agents, preferably anti-inflammatory arthritis agents. For example, in one embodiment the anti-inflammatory arthritis agent is administered separately by injection and the compound of the invention is administered orally, concurrently or sequentially.

Pharmaceutical Compositions and Dosage Forms

In a preferred embodiment, the compound is incorporated in a pharmaceutical composition that includes a pharmaceutically acceptable carrier. Advantageously, the composition may further include one or more anti-inflammatory arthritis agents. The anti-inflammatory arthritis agent can be any agent useful in treating inflammatory arthritis. Preferably the inflammatory arthritis agent is an analgesic, a COX-2 inhibitor, a corticosteroid, non-steroidal anti-inflammatory drug (NSAID); a disease modifying anti-rheumatic drug (DMARD); or a biologic disease modifying anti-rheumatic drug (biologic DMARD). In an alternative embodiment, the anti-inflammatory arthritis agent is separate.

Examples of preferred analgesic include: acetaminophen, aspirin, codeine, propoxyphene, fentanyl, PALLADONE® (generic name: hydromorphone), morphine, morphine sulfate, OXYCONTIN® (generic name: oxycodone), aspirin, pentazocine, tramadol, hydrocodone, naproxen, indomethacin, ibuprofen, fenoprofen, ketorolac tromethamine, choline magnesium trisalicylate, rofecoxib, and combinations thereof.

Examples of preferred COX-2 inhibitors include: rofecoxib, valdecoxib, parecoxib, etoricoxib, celecoxib, and combinations thereof.

Examples of preferred corticosteroids include: betamethasone, cortisone, dexamethasone, hydrocortisone, methylprednisolone, prednisolone, prednisone, triamcinolone, and combinations thereof.

Examples of preferred NSAIDs include: salicylate, arylalkanoic acid, 2-arylpropionic acid, N-arylanthranilic acid, oxiam, coxib, sulphonanilide, and combinations thereof.

Examples of preferred DMARDs and biological DMARDS include: hydroxychloroquine, chloroquine, leflunomide, methotrexate, sulfasalazine, gold, gold thiomalate, aurothioglucose, auranofin, azathioprine, cyclophosphamide, anti-tumor necrosis factor (anti-TNF, e.g., etanercept, infliximab, and adalimumab), anti-IL-1, Anti-CD20, anakinra, and combinations thereof.

In another preferred embodiment pharmaceutical composition comprises NATURA-α and/or NATURA. Typically the pharmaceutically acceptable carrier is an inert diluent.

The pharmaceutical compositions of the invention can take a variety of forms adapted to the chosen route of administration as discussed above. Those skilled in the art will recognize various synthetic methodologies that may be employed to prepare non-toxic pharmaceutically acceptable compositions of the compounds described herein. Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

Pharmaceutical compositions can be used in the preparation of individual dosage forms. Consequently, pharmaceutical compositions and dosage forms of the invention comprise the active ingredients disclosed herein. The notation of "the compound" signifies the compounds of the invention described herein or salts thereof. Pharmaceutical compositions and dosage forms of the invention can further comprise a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which an active ingredient is administered. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. In addition, other excipients can be used.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their route of administration and animal being treated. For example, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., Remington's Pharmaceutical Sciences, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

For a particular condition or method of treatment, the dosage is determined empirically, using known methods, and will depend upon facts such as the biological activity of the particular compound employed, the means of administrations, the age, health and body weight of the host; the nature and extent of the symptoms; the frequency of treatment; the administration of other therapies and the effect desired. Hereinafter are described various possible dosages and methods of administration with the understanding that the following are intended to be illustrative only. The actual dosages and method of administration or delivery may be determined by one of skill in the art.

Dosage levels of the order of from about 0.1 mg to about 250 mg per kilogram of body weight per day, more preferably from about 5 mg to about 150 mg per kilogram of body weight per day, and even more preferably between 5 mg to about 100 mg are useful in the treatment of arthritis in human. Dosage unit forms will generally contain between from about 1 mg to about 100 mg of the compound.

For illustrative purposes, dosage levels of the administered active ingredients in animals may be: intravenous, 0.01 to about 2 mg/kg; intramuscular, 0.05 to about 5 mg/kg; orally, 0.05 to about 100 mg/kg; intranasal instillation, 0.5 to about 10 mg/kg; and aerosol, 0.5 to about 100 mg/kg of host body weight. The dose level is usually about 10 times less in human than other animals.

Frequency of dosage may also vary depending on the compound used and whether an extended release formulation is used. However, for treatment of most disorders, a dosage regimen of 3 times daily or less is preferred. In a preferred embodiment, the treatment scheme is one time daily or less.

Preferably the compound is administered to the animal for a period of at least one week, more preferably for at least a month, and even more preferably for at least 45 or at least 60 days. Applicants have discovered benefits of continuous extended administration of the compound to the animal being treated. In certain embodiments, administration may be for at least six month, at least a year or even longer. For certain arthritic conditions, the treatment may require continuous administration during the life of the animal being treated. Administration can be prior to, during, or after the induction phase of the inflammatory arthritis has occurred. Preferably administration of the compound is prior to or during the induction phase.

Expressed in terms of concentration, a compound may be present in the compositions of the present invention for localized use about the cutis, intranasally, pharyngolaryngeally, bronchially, intravaginally, rectally, or ocularly in concentration of from about 0.01 to about 30% w/w of the composition; preferably about 1 to about 20% w/w of the composition; and for parenteral use in a concentration of from about 0.05 to about 10% w/v of the composition and preferably from about 1 to about 10% w/v.

Preferred compounds of the invention to be used in the compositions will have desirable pharmacological properties that include, but are not limited to, oral bioavailability, low toxicity, low serum protein binding and desirable in vitro and in vivo half-lives.

Assays may be used to predict these desirable pharmacological properties. Assays used to predict bioavailability include transport across human intestinal cell monolayers, including Caco-2 cell monolayers. Toxicity to cultured hepatocycles may be used to predict compound toxicity.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, Natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103 and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an active ingredient, anhydrous lactose, microcrystalline cellulose, polyvinylpyrrolidone, stearic acid, colloidal anhydrous silica, and gelatin.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous, bolus injection, intramuscular, and intraarterial. Because their administration typically bypasses patients' Natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences, 16th and 18th eds., Mack Publishing, Easton Pa. (1980 & 1990).

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts of the active ingredients can be used to further adjust the properties of the resulting composition.

The present invention will now be illustrated by the following non-limiting examples. It is to be understood that the foregoing describes preferred embodiments of the present invention and that modifications may be made therein without departing from the spirit or scope of the present invention as set forth in the claims.

EXAMPLES

Example 1

Short Term Treatment 1.1 Animal Model

Among the numerous experimental disease models mimicking rheumatoid arthritis (RA), Collagen-induced arthritis (CIA) in mice (Anthony and Haqqi 1999; Fournier 2005) is widely used to better define the pathogenic mechanisms and serves as vehicle to test novel therapeutic approaches. Collagen II-specific T cell clone was identified to be involved in arthritis induction. Considerable literature converged to point to a crucial pathogenic role for TNF-α, IL-1β and IL-6 in CIA model and such studies largely contributed to the successful development of anti-TNF-α therapies in RA. Therefore, it can be anticipated that NATURA-α (Meisoindigo) and NATURA will exert a beneficial preventive and therapeutic effects on inflammatory joint pathology.

Collagen-induced arthritis (CIA) was carried out in DBA/1 male mice following the standard protocol (Boissier, Feng et al. 1987). Briefly, for the first experiment: mice were primed with 100 μg bovine CII emulsified in complete Freund adjuvant (CFA) at day 0, and challenged with the same antigen dose in incomplete Freund adjuvant (IFA) three weeks later (FIG. 1 below).

1.2 Short-Term Treatment with NATURA-α Delays the Onset of CIA in Mice 1.2.1 Experimental Design The effect of preventive treatment with NATURA-α was tested in standard CIA protocol described above. NATURA-α suspension was prepared in water-based vehicle containing 0.5% propylene glycol and mice were treated by gavage with NATURA-α (or vehicle) at doses of 50 mg/kg and 100 mg/kg respectively as indicated. The Experimental protocol for the treatment of CIA with NATURA-α (or vehicle) is shown in FIG. 1. Experimental protocol for treatment of CIA with gavage of mice was performed twice for five consecutive days: first, at priming and second, at challenge with CII. After the last administration of the drug, mice were dispatched in order to get two mice from each group per cage.

The experiment included three control and two experimental groups (n=10/group) as follows:

(1) Naive mice treated with NATURA-α's vehicle
(2) CII-immunized mice treated with NATURA-α's vehicle
(3) Naive mice treated with the higher dose of NATURA-α (100 mg/Kg/dose)
(4) CII-immunized mice treated with NATURA-α dose 1 (100 mg/Kg/dose)
(5) CII-immunized mice treated with NATURA-α dose 2 (50 mg/Kg/dose)

The weight of the mice was recorded weekly from day 0 until the end of the experiment. Assessment of arthritis was performed by blind evaluation of clinical arthritis during the course of CIA three times per week. Data for individual mouse were expressed as:

(1) incidence of clinical arthritis
(2) onset of joint inflammation
(3) severity of arthritis (kinetics of arthritic scores and maximal score reached during the course of CIA). Means±SEM were calculated for each group.

1.2.2 Effect of Treatment with NATURA-α on CIA Clinical Parameters

As expected, control naive mice did not exhibit any sign of inflammatory arthritis whether or not they were given NATURA-α. Conversely, CII-immunized positive controls (fed with vehicle) developed severe arthritis as from day 28 post-priming (FIG. 2).

Figure 2:
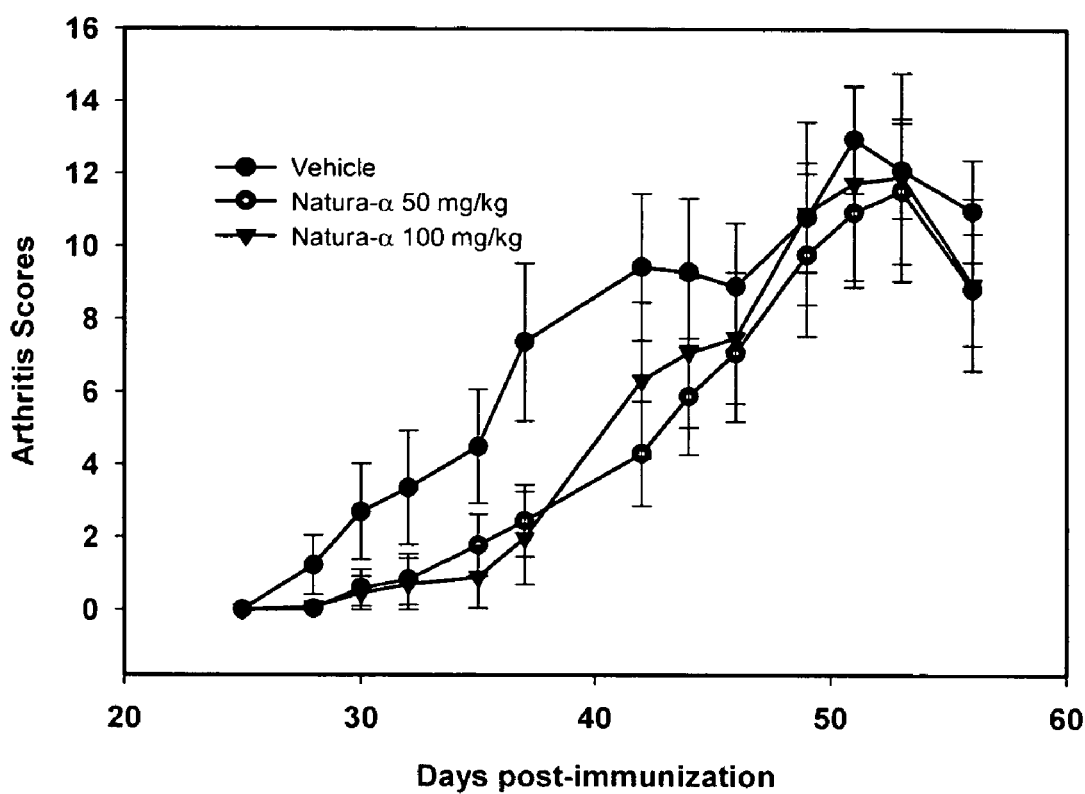
FIG. 2 shows the effect of oral administration of NATURA-α on CIA development. Blind monitoring of macroscopic signs of inflammation allowed determination of a clinical arthritis score for each mouse and evaluation of the kinetics of arthritis severity in the different groups. Data are mean±SEM of 10 mice/group.

Treatment with either dose of NATURA-α (50 and 100 mg/kg), following the regimen described in FIG. 1, induced a protective effect during early phases of clinical symptoms (FIG. 2). Indeed, significant differences (p<0.05, Mann-Whitney test) between "NATURA-α 100"-treated and control mice were observed from day 30 to day 37 post-immunization. However, the beneficial action of the drug was transient and fully abrogated by day 51. Data obtained with the dose of 50 mg/kg were very similar. No significant difference in efficacy between two-dose groups, indicates that the therapeutic effect of NATURA-α at 50 may have already reached the maximal.

TABLE 1

Effect of treatment with NATURA-α on various arthritis parameters. Data are mean ± SEM of 10 mice/group.

| Treatment groups | Incidence of CIA n (%) | Onset (days) | Maximal severity* |
|---|---|---|---|
| CII + vehicle | 10/10 (100%) | 36.2 ± 2.2 | 13.9 ± 1.5 |
| CII + NATURA-α (100 mg/Kg) | 8/10 (80%) | 39.9 ± 1.8 | 15.7 ± 2.6 |
| CII + NATURA-α (50 mg/Kg) | 8/10 (80%) | 39.5 ± 2.4 | 14.9 ± 0.9 |

*The maximal severity is the highest clinical score reached during CIA course by each affected mouse.

Detailed analysis of various CIA parameters confirmed the above conclusions: CIA occurred with lower incidence and moderately delayed onset in both groups given NATURA-α in comparison to control group (Table 1). Nevertheless, the NATURA-α-treated mice that developed arthritis exhibited clinical symptoms with identical severity than the control animals as evidenced by the maximal scores observed.

The findings provide evidence that oral administration of NATURA-α, following a preventive therapeutic protocol, ameliorates CIA in DBA/mice. The preventive effect was observed in groups of 10 mice and confirmed by converging data using several parameters of CIA. Furthermore, the reliability of the results is ensured by both dispatching mice from different groups in a cage and monitoring the development of clinical symptoms by blind evaluation. Beneficial effect elicited by NATURA-α was manifested by a delayed onset of arthritis and a modest decrease in the incidence. Thus, compared to controls, twenty percent less mice exhibited symptoms of inflammation later. However, once the first signs of arthritis occurred, severe inflammation progressed as rapidly as in vehicle-treated mice. Drug tolerance was good although a significant weight loss was observed after the first round of treatment probably due to stress as a result of gavage.

Example 2

Long Term Treatment

Continuous Treatment with NATURA-α Significantly Reduces Incidence and Severity of CIA and Improves General Health in Mice The schedule used for a treatment is known to be a critical factor for successful therapy. In example 1, it was chosen to administer NATURA-α for five consecutive days concomitantly to stimulate an immune responses i.e., at priming and challenging with CII. The fact that the drug-induced inhibitory effect was transient in this experiment is likely due the biological half-life of NATURA-α being approximately 10 hours, thereby the disease flares up and therefore, long lasting treatment or additional rounds of therapy would be required to improve the efficacy of NATURA-α in CIA.

2.1 Experimental Design

CIA was performed in DBA/1 male mice following the same standard protocol as described in example 1 above. Mice were treated orally by gavage with NATURA-α (or vehicle) as described below.

The experiment included one control and three experimental groups (n=10/group) as follows (it is important to note there was no positive treatment control group due to lack of available effective drug for this model):

(1) CII-immunized mice treated with NATURA-α's vehicle (2) CII-immunized mice treated with NATURA-α 50 mg/Kg, schedule 1

(3) CII-immunized mice treated with NATURA-α 50 mg/Kg, schedule 2

(4) CII-immunized mice treated with NATURA-α 50 mg/Kg, schedule 3

Treatments consisted of gavages three times per week at dose of 50 mg/Kg of NATURA-α (or vehicle) following three different regimens:

Schedule 1: from day 0 to day of sacrifice
Schedule 2: from day 21 to day of sacrifice
Schedule 3: from day 35 to day of sacrifice The weight of the mice was recorded weekly and assessment of arthritis was performed by blind evaluation of clinical arthritis during the course of CIA three times per week until day 56 post-priming. Data for individual mouse were expressed as:

(1) Incidence of clinical arthritis
(2) Onset of joint inflammation
(3) Severity of arthritis (kinetics of arthritic scores and maximal score reached during the course of CIA). Means±SEM were calculated for each group.

2.2 Continuous Treatment with NATURA-α Improves General Health of CIA Mice

Figure 3:
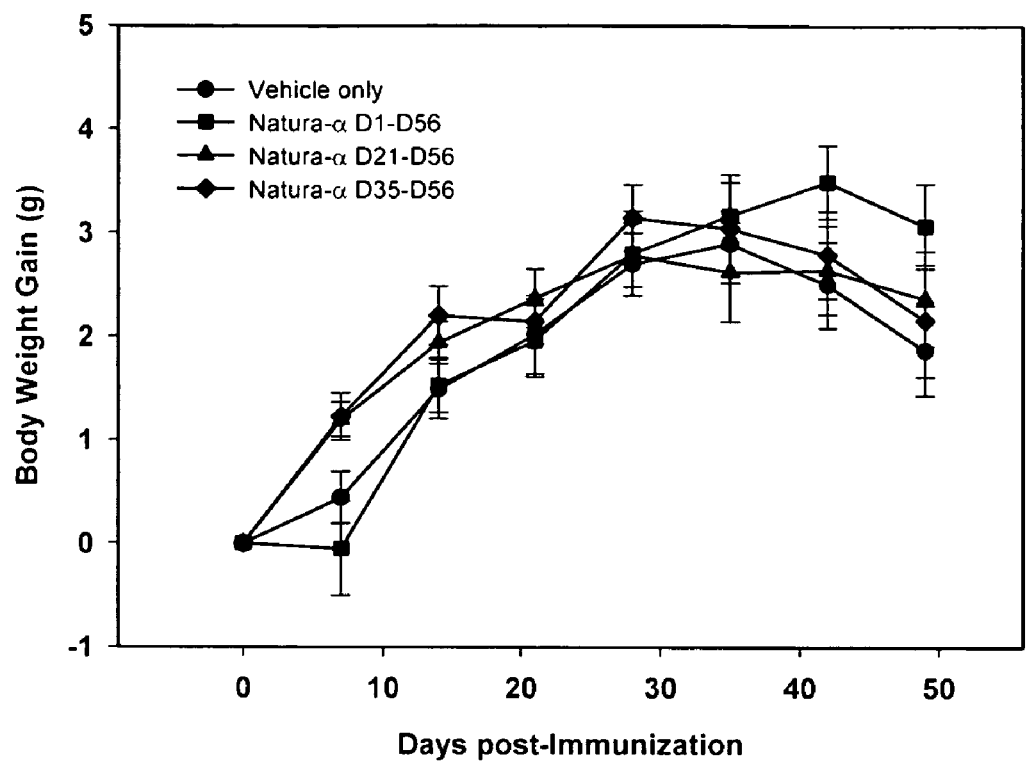
FIG. 3 shows a follow up of mouse body weight in the different treatment groups. Data show the treatment-induced differences in weight from day 0 and are expressed as mean±SEM of 10 mice in each group. Statistical analysis using the Student's t test: * p<0.05 (Vehicle-treated group vs. either NATURA-α late-treatment group); ** p<0.02 (NATURA-α DI-60 vs. either late-treatment group).
Figure 4:
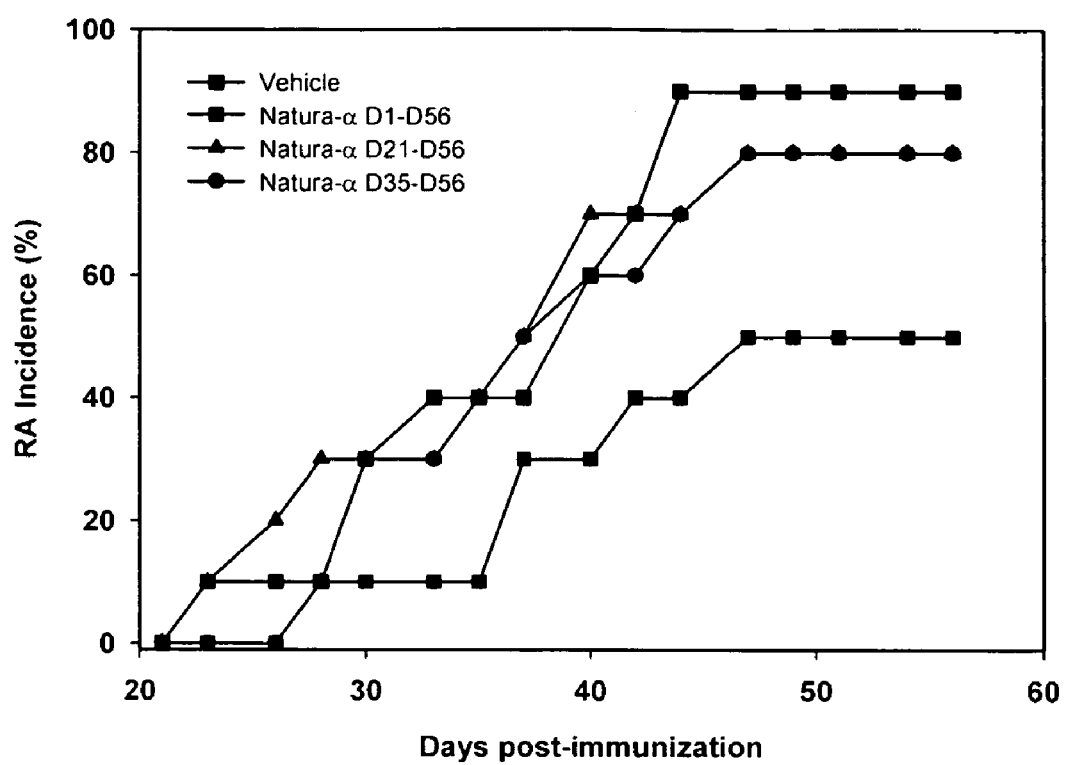
FIG. 4 shows time course of CIA incidence in NATURA-α-treated mice according to the regimen used for treatment. Mice were monitored for clinical signs of arthritis as from day of antigenic challenge (three weeks post-priming) and the day of onset was recorded. Data are percent of affected mice in each group as a function of time after immunization.

All the mice were weighted before immunization and then at weekly intervals. FIG. 3 shows that, during the first week of treatment with either NATURA-α or its vehicle, the growth of mice was altered since their weight increase was significantly lower than the two other untreated groups (p<0.02 and p<0.05 for NATURA-α and vehicle, respectively). These findings may result from the stress caused by the first gavages. Thereafter, treated mice progressively recovered to reach weights almost identical to those of the other groups by day 21. It is interesting to note that, in the group treated as from day 0 with NATURA-α, mice gained weight until day 42 while in the other groups the growth was stopped and mice started to slim down by day 28 due to CIA-induced systemic effects (FIG. 4). The finding may result from an overall improvement of health in related to NATURA-α treatment.

2.3 Continuous Treatment with NATURA-α Dramatically Decreases the Incidence of the Disease In the vehicle-treated group, the incidence of arthritic mice rapidly increased and reached a maximum of 90% by day 44, thus exhibiting the classical features of CIA model (FIG. 4). Notably, in the group of mice that were treated with 50 mg/Kg NATURA-α all over the experiment (for 8 weeks starting at priming), a fewer mice were affected at anytime and in final the cumulative incidence was markedly lower (50% as compared 90% in untreated control). The time course of CIA incidence in NATURA-α-treated mice according to the regimen used for treatment. Mice were monitored for clinical signs of arthritis as from day of antigenic challenge (three weeks post-priming) and the day of onset was recorded. Data are percent of affected mice in each group as a function of time after immunization. Regarding the two other treatment groups in which initiation of the treatment was delayed, there was no statistically difference with the controls in terms of both kinetics and total number of mice that developed CIA (FIG. 4).

Figure 5:
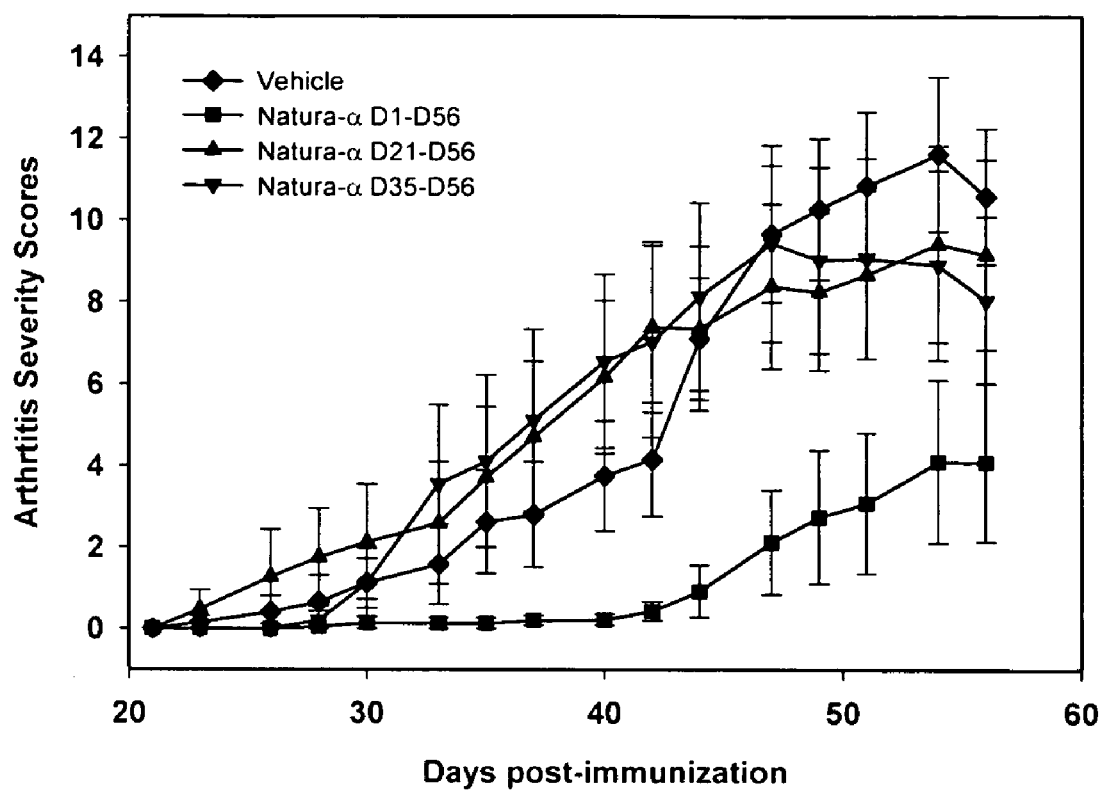
FIG. 5 shows the effect of oral administration with NATURA-α on CIA development. Blind monitoring of macroscopic signs of inflammation was performed to determine a clinical arthritis score for each mouse and to evaluate the kinetics of arthritis severity in the different groups. Data are mean±SEM of 10 mice/group. * p<0.02; # p<0.01 vs. vehicle-treated group (Student's t test).

2.4 Continuous Treatment with NATURA-α Significantly Delays the Onset and Reduces Severity of the Disease Kinetic blind scoring of macroscopic manifestations for each mouse allowed to determine the average course of CIA in the four groups (FIG. 5). Severe arthritis developed in CII-immunized positive controls (fed with vehicle all along the experiment) with onset as from day 26 post-priming and maximal arthritis scores by day 50.

When the treatment with NATURA-α was initiated at time of immunization and given throughout the experiment course, CIA was significantly suppressed all along the observation period (FIG. 5). Notably, not only were the number of fully protected mice higher in this group compared to the other groups but the arthritis onset occurred at a later time and the disease was less severe (Table 2).

Late treatment with NATURA-α starting from day 21 or day 35 till the end of the experiment, resulted in a slightly lower incidence of affected mice (80% vs. 90%). In those two groups, clinical scores were similar to the control group. While the disease scores in control group continue to increase from day 21 to day 55 and more rapidly from day 42 to day 55, the increase of disease score of NATURA-α D21-56 group slows down from day 42 (only after 9 treatments) and the disease score of NATURA-α D35-56 group starts to decrease since day 48 (only after 6 treatments) (FIG. 5). Therefore, NATURA-α is effective even after severe arthritis is already developed.

TABLE 2

Effect of treatment with NATURA-α following different regimens on various arthritis parameters. Data are mean ± SEM of n diseased mice/group.

| Treatment groups | Incidence of CIA n (%) | Onset (days) | Maximal severity* |
|---|---|---|---|
| CII + vehicle | 9/10 (90%) | 36.2 ± 2.5 | 13.8 ± 1.6 |
| CII + NATURA-α (D1-56) | 5/10 (50%) | 38.2 ± 3.2 | 8.8 ± 3.2 |

TABLE 2-continued

Effect of treatment with NATURA-α following different regimens on various arthritis parameters. Data are mean ± SEM of n diseased mice/group.

| Treatment groups | Incidence of CIA n (%) | Onset (days) | Maximal severity* |
|---|---|---|---|
| CII + NATURA-α (D21-56) | 8/10 (80%) | 34.5 ± 2.9 | 13.5 ± 2.3 |
| CII + NATURA-α (D35-56) | 8/10 (80%) | 36.4 ± 2.5 | 12.7 ± 2.5 |

*The maximal severity is the higher clinical score reached during CIA course by each affected mouse.
**$P < 0.05$ Further detailed analysis of data from the early treatment group revealed that five of ten mice never exhibited any sign of inflammation in the four paws within 57 days following priming and challenging with CII and two had swelling of only one and three digits, respectively. In the remaining three mice, the first clinical symptoms consisted in moderate inflammation of some digits that lasted for one to two weeks before flare up of the disease had extended to other joints such as tarsus, ankles or carpus. This slow course of severity at onset of CIA sharply contrasted with that of mice in the vehicle-treated group in which the disease developed aggressively shortly after it was diagnosed. However, once the inflammatory process was triggered in mice receiving NATURA-α, the severity of arthritis progressively increased and reached similar magnitude than in controls (Table 3).

TABLE 3

Detailed analysis of arthritis severity according to the treatment with NATURA-α. The severity of arthritis is the higher clinical score reached during CIA course by each affected mouse in the subgroup considered. Data are mean ± SEM of the indicated number of mice/subgroup.

| Treatment groups | Number of mice | No arthritis | Mild arthritis (affecting only digits) | | Slowly developing arthritis | | Full blown arthritis | |
|---|---|---|---|---|---|---|---|---|
| | N | N | n | Severity | n | Severity | n | Severity |
| Vehicle | 10 | 1 | 0 | — | 1 | 7.7 | 8 | 14.5 ± 1.6 |
| NATURA-α (D1-56) | 10 | 5 | 2 | 1.1 ± 0.7 | 3 | 14.0 ± 0.9 | 0 | — |
| NATURA-α (D21-56) | 10 | 2 | 1 | 2.5 | 0 | — | 7 | 15.1 ± 1.8 |
| NATURA-α (D35-56) | 10 | 2 | 1 | 0.4 | 0 | — | 7 | 14.5 ± 2.1 |

Taken together, these findings point to a marked protective effect of NATURA-α on CIA provided that the drug is administered during the induction phase of the disease. If the treatment starts when the immune system is boosted (on day 21) or around the onset of clinical signs of arthritis (on day 35), NATURA-α may still have certain therapeutic effects.

2.5 NATURA-α Inhibits Humoral Response in CIA Mice 2.5.1 Kinetics of Humoral Responses to CII Immunization with CII elicits a specific humoral response in all mice. Although levels of anti-CII antibodies are not strictly correlated to arthritis scores, they are usually high in sera from severely diseased mice. Thus, anti-CII IgG have been measured in all the mice on days 20 (before challenge with CII), 40 (during CIA course) and at sacrifice of mice.

Figure 6:
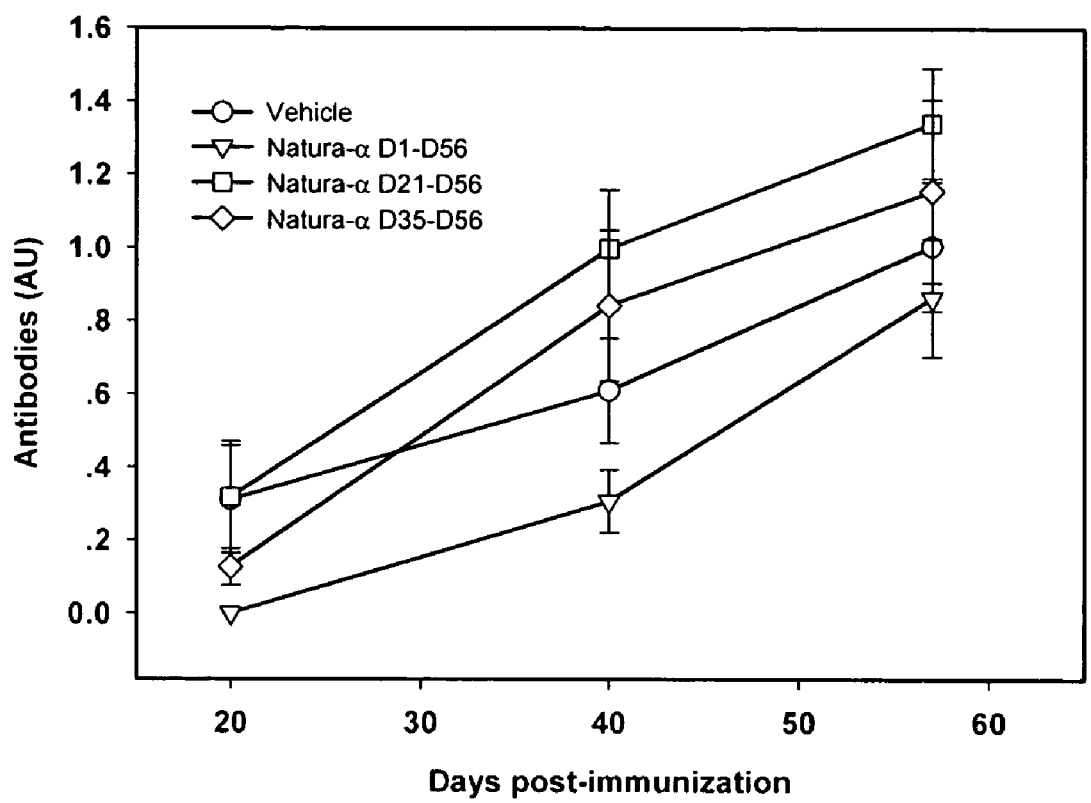
FIG. 6 shows the kinetics of circulating anti-CII antibody levels in CII-immunized mice treated with NATURA-α or vehicle. Sera from individual mouse were collected at days 20, 40 and 57 after immunization and CII-specific IgG were measured in serial dilutions of the serum using ELISA. Data are mean±SEM of 10 mice/group.

In all the groups, titers of anti-CII IgG increased along with time, however, the levels were consistently lower in the mice treated with NATURA-α as from day of immunization compared to all other groups (FIG. 6). On day 20, just before antigenic boost, none of NATURA-α-treated mice had detectable amounts of circulating antibodies whereas, in the other groups (either receiving vehicle or untreated), 4 to 5 of 10 mice secreted variable levels of anti-CII IgG. The CII specific humoral response in mice given an early treatment with NATURA-α remained impaired on day 40 when only three mice had mild inflammation of digits but tended to normalize at the end of the experiment (FIG. 6). These findings indicate that, when it was administered at the moment of CIA induction, NATURA-α quantitatively reduced the secretion of anti-CII antibodies.

2.5.2 Humoral Inhibition by NATURA-α Significantly Affects the IgG2a Isotype

To study whether the drug also altered qualitatively the humoral response, levels of CII-specific antibodies expressing IgG1 and IgG2a isotypes were determined in samples collected on day 40 post priming. In line with the data described above, levels of anti-CII total IgG were impaired in the group that underwent early treatment with NATURA-α. Interestingly, the drop in antibody response significantly affected the IgG2a isotype (p=0.01) whereas it weakly reduced the IgG1 (FIG. 5). Regarding the two late-treatment schedules, CII-specific IgG2a levels were identical to those in the control group and IgG1 were rather increased. Since antibody production of IgG2a and IgG1 isotypes are known to be associated with Th1 and Th2 responses, respectively, the present findings teach and support the finding that NATURA-α can induce a beneficial shift from a Th1 towards a Th2 response.

Figure 7:
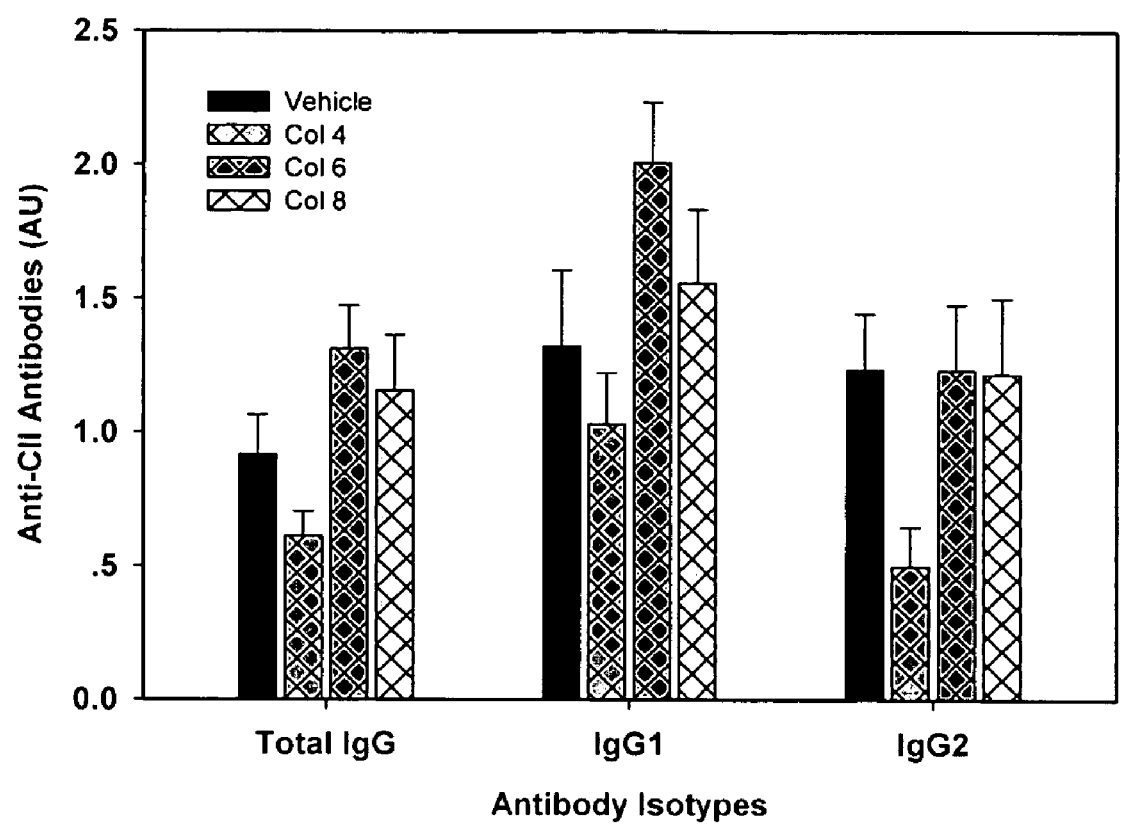
FIG. 7 shows the qualitative humoral response to CII in immunized mice treated with NATURA-α following different regimens. Levels of anti-CII antibodies (total IgG, IgG1 and IgG2a isotypes) were detected in sera from individual mouse collected on day 40 post-priming using ELISA. Data are mean±SEM of 10 mice/group. * p=0.01 vs. vehicle-treated group (Student's t test).

As shown in FIG. 7, qualitative humoral response to CII in immunized mice treated with NATURA-α following different regimens. Levels of anti-CII antibodies (total IgG, IgG1 and IgG2a isotypes) were detected in sera from individual mouse collected on day 40 post-priming using ELISA.

2.5.3 NATURA-α Involves In Vivo Expansion of Regulatory T Cells in the Spleen in Mice To explore whether the beneficial effect of NATURA-α on arthritis could be associated with late (at time of sacrifice) changes in T cells, the proliferative response to CII and the percentage of regulatory T (Treg) cells (defined as $CD4^+/CD25^+/Foxp3^+$) were evaluated in the spleen and lymph nodes of mice treated with NATURA-α as from day of immunization and compared to that of control mice. Three mice in each group were selected according to their clinical status: in the group given NATURA-α, two mice never exhibited macroscopic signs of inflammation and one had a high severity score of arthritis at time of sacrifice. In the control group, it was the reverse situation: two mice were severely affected and one never developed arthritis.

In all the mice tested from the two groups, specific proliferative responses to varying concentrations of CII were very low (if any) with proliferation indexes below 2 both in the spleen and lymph nodes (data not shown) indicating that CII-specific T cells could not be detected in the lymphoid organs two months after immunization. Regarding the detection of Treg cells, a mild increase (40%) of spleen CD4$^+$/CD25$^+$/Foxp3$^+$ were noted in all the mice treated with NATURA-α but not in lymph node cells. (Table 4).

TABLE 4

Determination of Treg cells in the spleen and lymph node cells of some mice selected at the end of the in vivo experiment according to their arthritis status during CIA course. Percentages of T reg (CD4$^+$/CD25$^+$/Foxp3$^+$)

| No. | Arthritis | Spleen | Lymph nodes |
|---|---|---|---|
| Vehicle-treated mice | | | |
| 1 | yes | 13.2 | 9.7 |
| 2 | yes | 10.2 | 9.1 |
| 3 | no | 7.6 | 9.9 |
| Mean ± SEM | | 10.3 ± 1.6 | 9.6 ± 0.3 |
| NATURA-α-treated (D1-56) mice | | | |
| 4 | no | 13.1 | 8.9 |
| 5 | no | 14.4 | 9.2 |
| 6 | yes | 14.9 | 11.1 |
| Mean ± SEM | | 14.1 ± 0.6 | 9.7 ± 0.7 |

Example 3

Effect of NATURA-α and NATURA on Treg In Vitro

To examine effects of NATURA-α and NATURA on induction of Treg cells and to compare their activity to immuno-suppressant Rapamycin, CD4 and CD25 double positive lymphocytes were selected from peripheral blood of MC patients (PBMC) by CD25 Microbeads (MACS, Miltenyi Biotec, Inc.) cultured with 1 μM of NATURA-α, NATURA or 5 ng/ml of Rapamycin. CD4$^+$25$^+$ fraction was cultured in ex-vivo medium with 5% human serum, IL2, and stimulatory beads conjugated with CD3 and CD28 monoclonal antibodies (cell: bead=1:4). Cell cultures were checked every 48 hours and cell densities were adjusted between 5e5 and 1e6 cell/ml. CD4$^+$25$^+$FoxP3$^+$ fractions (Treg) were analyzed by Flow cytometry (FCM) with phenotypical surface staining and FoxP3 intracellular staining (FITC anti-human FoxP3 Staining Set, eBioscience) at 10$^{th}$ and 20$^{th}$ day of culture.

Figure 8:
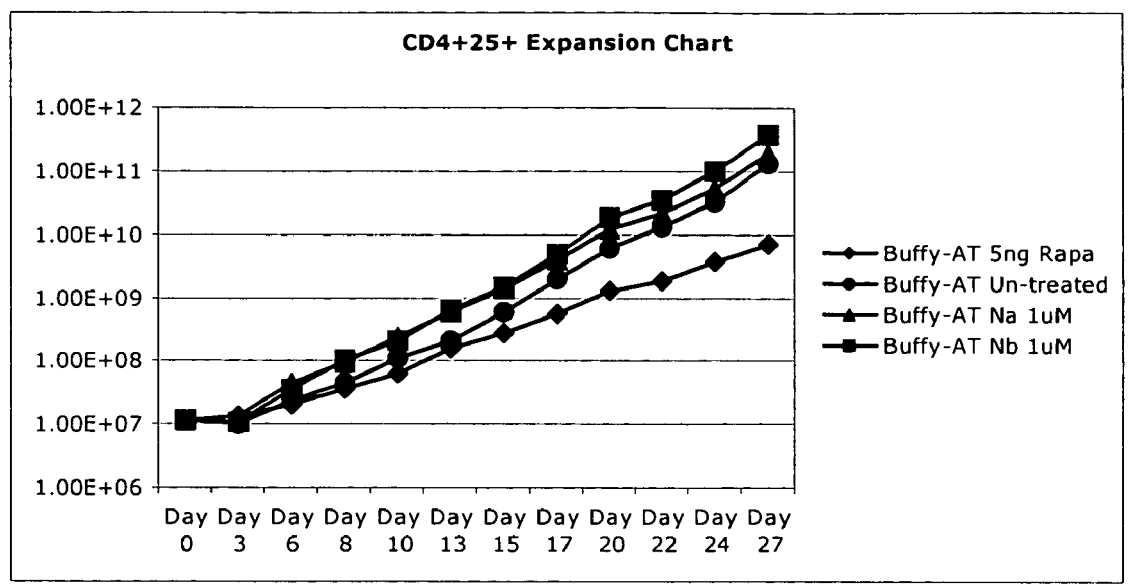
FIG. 8 shows the effects of NATURA-α, NATURA, and Rapamycin on $CD4^+CD25^+$ cell growth. Immuno-purified from peripheral blood of MC patients (PBMC) by CD25 microbeads were incubated with indicated concentrations of NATURA-α, NATURA, and Rapamycin, and the cell densities were examined every 48 or 72 hours.
Figure 9:
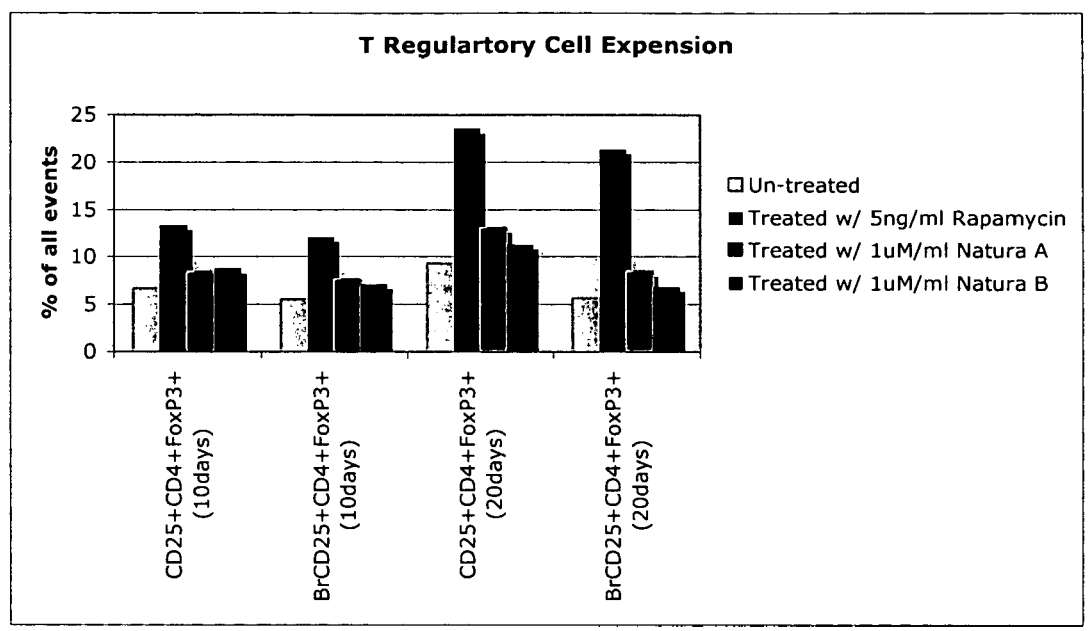
FIG. 9 shows the selective expansion of regulatory T cells (Treg) ($CD4^+CD25^+FoxP3^+$) cell population by NATURA-α, NATURA, and Rapamycin. Immuno-purified $CD4^+CD25^+$ T cells from PBMC were incubated with indicated concentrations of NATURA-α, NATURA, and Rapamycin in ex-vivo medium with 5% human serum, IL2, and stimulatory beads conjugated with CD3 and CD28 monoclonal antibodies. $CD4^+25^+FoxP3^+$ fractions (Treg) were examined by FCM with phenotypical surface staining and FoxP3 intracellular staining at day 10 and 20 of culture.

As shown in FIGS. 8 and 9, incubation of CD4$^+$25$^+$ cells with both NATURA-α and NATURA resulted in moderate expansion of Treg cells, which paralleled the in vivo findings that treatment of NATURA-α in CIA mice increased the Treg cell population (Table 4). It is noted that both NATURA-α and NATURA also produced moderate growth stimulation, which was different from conventional immuno-suppressant Rapamycin. While Rapamycin significantly stimulated Treg cell population, a strong growth inhibition of the CD4$^+$25$^+$ double positive T cells was also observed with Rapamycin (FIG. 8).

FIG. 9 shows the selective expansion of Treg (CD4$^+$CD25$^+$FoxP3$^+$) cell population by NATURA-α, NATURA, and Rapamycin. Immuno-purified CD4$^+$CD25$^+$ T cells from PBMC were incubated with indicated concentrations of NATURA-α, NATURA, and Rapamycin in ex-vivo medium with 5% human serum, IL2, and stimulatory beads conjugated with CD3 and CD28 monoclonal antibodies. CD4$^+$25$^+$FoxP3$^+$ fractions (Treg) were examined by FCM with phenotypical surface staining and FoxP3 intracellular staining at 10$^{th}$ and 20$^{th}$ day of culture.

Discussion

Inflammatory arthritis, e.g., RA, is a complex disease with a broad spectrum of manifestations. Many molecular and cellular components of immune system are involved in the pathogenesis. Clinical successes have validated cytokines, B cells as well as T cells as targets for developing new therapeutics for RA. Recently identified T-regulatory cells have an important role in peripheral tolerance. Treg cells are able to suppress antigen specific immune response in vitro as well as in vivo (Groux, O'Garra et al. 1997). Treg cells control the immune response to a variety of antigens, including self-antigens, and may offer opportunities to intervene in the course of autoimmune diseases. However, little is known about mechanisms controlling the peripheral expansion of CD4$^+$, CD25$^+$ Treg. Efforts have been made to generating efficient Treg cells ex vivo, which could be used as an attractive therapeutic tool in the future. Some endogenous molecules such as IL10, TGFβ induce Treg population while TNFα inhibit suppressive function of regulatory T cells in vivo (Valencia, et al. 2006). No small molecule with therapeutic potential has been shown to be able to expand regulatory T cells in vivo.

In this application, we provided evidence that the compounds of the invention, e.g., NATURA-α, are effective in treatment and prevention of inflammatory arthritis in a sophisticated collagen II induced arthritis model through inhibiting antigen-induced humoral response, rebalancing Th1 and Th2 cells. We have shown that it significantly reduces the incidence and severity of arthritis in CIA model. Moreover, we also demonstrated that the compounds of the invention are able to expand regulatory T cells (CD4$^+$CD25$^+$FoxP3$^+$) in vivo in animals (CIA). We further provide in vitro studies showing the ability of the compounds to expand regulatory T cells in humans (peripheral blood from MC patients). This provides evidence that the compounds of the invention, e.g., NATURA-α, can be successfully used for treatment of inflammatory arthritis, and especially where cytokine, humoral response or regulatory T cells are involved.

The preceding technological disclosure describes illustrative embodiments of the method of treating inflammatory arthritis and is not intended to limit the present invention to these precise embodiments. Further, any changes and/or modifications, which may be obvious by one with ordinary skill in the related art, including but not limited to pharmaceutical salt derivatives or non-functional changes are intended to be included within the scope of the invention.

REFERENCES

Anthony, D. D. and T. M. Haqqi (1999). "Collagen-induced arthritis in mice: an animal model to study the pathogenesis of rheumatoid arthritis." *Clin Exp Rheumatol* 17(2): 240-4.

Askling, J., C. M. Fored, et al. (2005). "Risks of solid cancers in patients with rheumatoid arthritis and after treatment with tumour necrosis factor antagonists." *Ann Rheum Dis* 64(10): 1421-6.

Boers, M. (2004). "Glucocorticoids in rheumatoid arthritis: a senescent research agenda on the brink of rejuvenation?" *Best Pract Res Clin Rheumatol* 18(1): 21-9.

Boissier, M. C., X. Z. Feng, et al. (1987). "Experimental autoimmune arthritis in mice. I. Homologous type II collagen is responsible for self-perpetuating chronic polyarthritis." *Ann Rheum Dis* 46(9): 691-700.

Bongartz, T., A. J. Sutton, et al. (2006). "Anti-TNF antibody therapy in rheumatoid arthritis and the risk of serious infections and malignancies: systematic review and meta-analysis of rare harmful effects in randomized controlled trials." *Jama* 295(19): 2275-85.

Borchers, A. T., C. L. Keen, et al. (2004). "The use of methotrexate in rheumatoid arthritis." *Semin Arthritis Rheum* 34(1): 465-83.

Caporali, R. and C. Montecucco (2005). "Cardiovascular effects of coxibs." *Lupus* 14(9): 785-8.

Chakravarty, E. F., K. Michaud, et al. (2005). "Skin cancer, rheumatoid arthritis, and tumor necrosis factor inhibitors." *J Rheumatol* 32(11): 2130-5.

Fournier, C. (2005). "Where do T cells stand in rheumatoid arthritis?" *Joint Bone Spine* 72(6): 527-32.

Groux, H., A. O'Garra, et al. (1997). "A CD4+ T-cell subset inhibits antigen-specific T-cell responses and prevents colitis." *Nature* 389(6652): 737-42.

Higashida, J., T. Wun, et al. (2005). "Safety and efficacy of rituximab in patients with rheumatoid arthritis refractory to disease modifying antirheumatic drugs and anti-tumor necrosis factor-alpha treatment." *J Rheumatol* 32(11): 2109-15.

Klippel, J. H. (2000). "Biologic therapy for rheumatoid arthritis." *N Engl J Med* 343(22): 1640-1.

Lawrence, R., C. G. Helmick, et al, (1998). "Estimates of the prevalence of arthritis and selected musculoskeletal disorders in the United States." *Arthritis & Rheumatism* 41:778-99.

Listing, J., A. Strangfeld, et al. (2005). "Infections in patients with rheumatoid arthritis treated with biologic agents." *Arthritis Rheum* 52(11): 3403-12.

Maini, R. N. and P. C. Taylor (2000). "Anti-cytokine therapy for rheumatoid arthritis." *Annu Rev Med* 51: 207-29.

Mencher, S. K. and L. G. Wang (2005). "Promiscuous drugs compared to selective drugs (promiscuity can be a virtue)." *BMC Clin Pharmacol* 5(1): 3.

Moreland, L. (2005). "Unmet needs in rheumatoid arthritis." *Arthritis Res Ther* 7 Suppl 3: S2-8.

Navarro-Sarabia, F., R. Ariza-Ariza, et al. (2006). "Adalimumab for treating rheumatoid arthritis." *J Rheumatol* 33(6): 1075-81.

Reimold, A. M. (2002). "TNFalpha as therapeutic target: new drugs, more applications." *Curr Drug Targets Inflamm Allergy* 1(4): 377-92.

Silman, A. J. and J. E. Pearson (2002). "Epidemiology and genetics of rheumatoid arthritis." *Arthritis Res* 4 Suppl 3: S265-72.

Symmons, D. P. and A. J. Silman (2006). "The world of biologics." *Lupus* 15(3): 122-6.

Wong, J. B. (2004). "Cost-effectiveness of anti-tumor necrosis factor agents." *Clin Exp Rheumatol* 22(5 Suppl 35): S65-70.

What is claimed is:

1. A method of treating rheumatoid arthritis comprising administering to an animal suffering from rheumatoid arthritis a therapeutically effective amount of at least one compound selected from the group consisting of: formulas (IV), (V), and (VI) respectively:

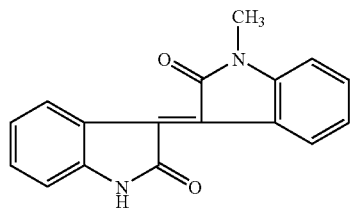

FORMULA (IV)

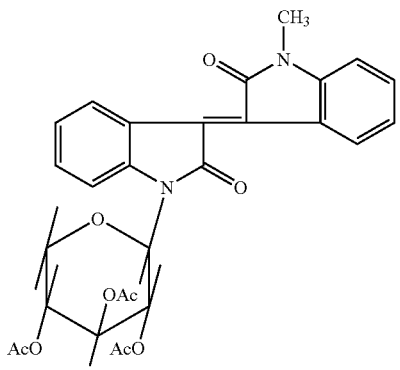

FORMULA (V)

wherein the amount is sufficient to treat the rheumatoid arthritis by inhibiting pro-inflammatory cytokine expression and/or by stimulating anti-inflammatory cytokines, but less than sufficient to substantially inhibit cyclin dependent kinases (CDKs).

2. The method of claim 1, wherein the compound is the compound of formula (IV):

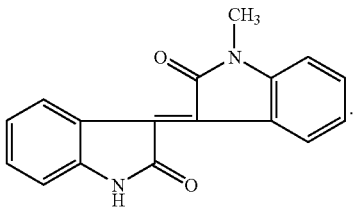

FORMULA (IV)

3. The method of claim 1, wherein the compound is administered during the induction phase of the rheumatoid arthritis.

4. The method of claim 3, wherein the animal is a human and the compound is administered orally, mucosally, parenterally, topically, or transdermally.

5. The method according to claim 4, wherein administration of the compound is in an amount of 5 to 100 mg/day.

6. The method of claim 1, wherein the animal is diagnosed with rheumatoid arthritis and the compound is administered in conjunction with an agent selected from the group consisting of: an analgesic, a COX-2 inhibitor, a corticosteroid, non-steroidal anti-inflammatory drug (NSAID); a disease modifying anti-rheumatic drug (DMARD); and a biologic disease modifying anti-rheumatic drug (biologic DMARD).

7. The method of claim 6, wherein the agent is an analgesic selected from the group consisting of: acetaminophen, aspirin, codeine, propoxyphene, fentanyl, hydromorphone, morphine, morphine sulfate, oxycodone, pentazocine, tramadol, hydrocodone, naproxen, indomethacin, ibuprofen, fenoprofen, ketorolac tromethamine, choline magnesium trisalicylate, and combinations thereof.

8. The method of claim 6, wherein the agent is selected from the group consisting of: rofecoxib, valdecoxib, parecoxib, etoricoxib, celecoxib, betamethasone, cortisone, dexamethasone, hydrocortisone, methylprednisolone, prednisolone, prednisone, triamcinolone, salicylate, arylalkanoic acid, 2-arylpropionic acid, N-arylanthranilic acid, oxiam, coxib, sulphonanilide, hydroxychloroquine, chloroquine, leflunomide, methotrexate, sulfasalazine, gold, gold thiomalate, aurothioglucose, auranofin, azathioprine, cyclophosphamide, anti-tumor necrosis factor (anti-TNF), etanercept, infliximab, and adalimumab, anti-IL-1, anti-CD20, anakinra, or combinations thereof.

9. The method of claim 1, wherein administration of the compound is in an oral formulation and is administered for a period of at least 45 days.

10. The method according to claim 1, wherein at least two compounds are administered concurrently or sequentially in an extended release formulation.

11. The method according to claim 1, wherein the compound is administered in a pharmaceutical composition comprising the compound and a pharmaceutically acceptable carrier.

12. The method according to claim 1, wherein the compound is administered at a concentration sufficient to inhibit at least one cytokine selected from the group consisting of IL-1$\alpha$, $\beta$, IL-2, IL-3, IL-6, IL-7, IL-9, IL-12, IL-17, IL-18, TNF-$\alpha$, LT, LIF, Oncostatin, or IFNc1$\alpha$, $\beta$, $\gamma$; and/or stimulate expression of at least one cytokine selected from the group consisting of IL-4, IL-10, IL-11, W-13 or TGF$\beta$.

13. The method of claim 1, wherein the compound is administered in an amount sufficient to modulate cytokines TNF-$\alpha$, IL-1$\beta$, IL-6, and IL-10.

* * * * *